US011492380B2

(12) United States Patent
Lyman et al.

(10) Patent No.: US 11,492,380 B2
(45) Date of Patent: Nov. 8, 2022

(54) PEPCON PROTEOMICS STANDARDS AND METHODS OF USE

(71) Applicant: Lawrence Livermore National Security, LLC, Livermore, CA (US)

(72) Inventors: Mathew Gerald Lyman, Brentwood, CA (US); Deon S. Anex, Livermore, CA (US); Bonnee Rubinfeld, Danville, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 208 days.

(21) Appl. No.: 16/908,521

(22) Filed: Jun. 22, 2020

(65) Prior Publication Data

US 2021/0024590 A1     Jan. 28, 2021

Related U.S. Application Data

(60) Provisional application No. 62/877,995, filed on Jul. 24, 2019.

(51) Int. Cl.
  *C07K 14/245*     (2006.01)
  *G01N 33/68*      (2006.01)

(52) U.S. Cl.
  CPC ....... *C07K 14/245* (2013.01); *G01N 33/6848* (2013.01)

(58) Field of Classification Search
  None
  See application file for complete search history.

(56) References Cited

U.S. PATENT DOCUMENTS

2007/0122425 A1*  5/2007  Keeler ............... C07K 14/195
                                                424/443

OTHER PUBLICATIONS

Nadler et al., "MALDI versus ESI: The Impact of the Ion Source on Peptide Identification," J. Proteome Res. (2017) 16(3):1207-1215.
Trevino et al. "Amino acid contribution to protein solubility: Asp, Glu, and Ser contribute more favorably than the other hydrophilic amino acids in RNase Sa," J. Mol. Biol. (2007) 366(2):449-460.

\* cited by examiner

*Primary Examiner* — Xiaoyun R Xu
(74) *Attorney, Agent, or Firm* — Perkins Coie LLP

(57) ABSTRACT

Described are methods, compositions, and devices for a concatemeric protein standard that behaves as a protein but transforms into single peptides upon digestion, which is optimized to function as a non-obtrusive process control for mass spectrometry analysis.

13 Claims, 10 Drawing Sheets

Specification includes a Sequence Listing.

US 11,492,380 B2

PEPCON PROTEOMICS STANDARDS AND METHODS OF USE

CROSS-REFERENCE TO RELATED APPLICATIONS

This application claims the benefit of U.S. Provisional Patent Application No. 62/877,995 filed on Jul. 24, 2019, the content of which is incorporated by reference in its entirety.

STATEMENT REGARDING FEDERALLY SPONSORED RESEARCH

The United States government has rights in this invention pursuant to Contract No. DE-AC52-07NA27344 between the U.S. Department of Energy and Lawrence Livermore National Security, LLC, for the operation of Lawrence Livermore National Laboratory.

TECHNICAL FIELD

This disclosure relates to peptide concatemers ("Pep-Cons") that behave as peptide species upon digestion, and to methods for generating and using these PepCons, for example as control standards in proteomics. In particular, this disclosure describes single peptide concatemers comprising multiple repeats of a single peptide sequence that are optimized for protein solubility and electrospray ionization ("ESI") for use as standards for protein mass spectrometry.

BACKGROUND

Proteomics is the large-scale study of proteins, which are often proteins contained within cells, tissues, or an entire organism. In order to study these proteins, scientists typically engage in the following four steps: (1) fractionate a complex mixture of unknown proteins; (2) digest those proteins into peptides; (3) utilize mass spectrometry to analyze the individual peptides; and (4) utilize bioinformatics methods to assemble the mass spectrometry data into identified proteins.

Several technologies exist for the absolute quantitation of peptides within a complex mixture. QconCAT technology is a recently developed technology for the absolute quantification of proteins of interest in a biological sample. Qcon-CAT technology relies on artificially created proteins that are concatenations of multiple different, isotopically labeled peptides. The peptides are selected based on the proteins of interest. Genes encoding the QconCAT protein are normally expressed in *Escherichia coli* (abbreviated as *E. coli*) host cells in the presence of media supplemented with isotope-labeled amino acids. The expressed QconCAT protein is then added to the protein mixture and digested alongside the analytes to create a set of isotopically labeled reference peptides. Because these isotopically labeled peptides are all at a 1:1 ratio and correspond to naturally occurring peptides in the biological sample, each peptide can be used as a standard for the absolute quantitation of all proteins of interest at once.

Although the QconCAT technology has utility for quantitation of known peptides in a mixture, it is not helpful for scientists who need a proteomics standard (1) that can be spiked into a protein mixture at an extremely low level, (2) that can be co-purified during sample fractionation, and (3) that is optimized for ESI used in mass spectrometry. Thus, there exists a need for an ideal standard protein that is large enough to behave as a protein but consists of multiple, concatenated copies of the same peptide, which, upon digestion, amplifies (e.g., >10-fold) into a detectable peptide species.

SUMMARY

This disclosure provides a novel approach for designing, generating, and using a concatemer protein containing multiple copies of a peptide optimized to serves as qualitative standards in proteomics.

In some aspects, the disclosure provides a peptide concatemer ("PepCon") comprising two or more copies of a peptide linked by a cleavage site.

In some aspects, the disclosure provides a composition comprising the PepCon according to any embodiment disclosed and described herein or any fragment thereof.

In some aspects, the disclosure provides an expression vector comprising a nucleotide sequence encoding the PepCon according to any embodiment disclosed and described herein, for example, the sequence set forth in SEQ ID NO. 2 or SEQ ID. NO. 14, or a variant thereof which is at least 80% homologous to SEQ ID NO. 2 or SEQ ID NO. 14.

In some aspects, the disclosure provides a peptide concatemer ("PepCon") having the sequence set forth in SEQ ID NO. 4 or SEQ ID NO. 10.

In some aspects, the disclosure provides a peptide having the sequence set forth in SEQ ID NO. 7.

In some aspects, the disclosure provides a method of generating a peptide concatemer ("PepCon"), comprising: (a) generating a vector comprising a nucleotide sequence encoding a PepCon, wherein the PepCon comprises two or more copies of a peptide linked by a cleavage site; and (b) expressing the PepCon from the nucleotide sequence. In some embodiments, the expressing step occurs in a host cell. In some embodiments, the expressing step occurs in an in vitro transcription/translation system. In some embodiments, the method further comprises purifying the PepCon.

In some aspects, the disclosure provides a method of using a qualitative control for protein mass spectrometry, comprising: (a) generating an analysis sample by combining a protein sample with a peptide concatemer ("PepCon"), wherein the PepCon comprises two or more copies of a peptide linked by a cleavage site; and (b) digesting the analysis sample with an agent capable of cleaving at the cleavage site. In some embodiments, the method further comprises analyzing the analysis sample by mass spectrometry.

In some embodiments, the PepCon further comprises an affinity tag. In some embodiments, the affinity tag is a FLAG, HA, His, myc, chitin binding protein (CBP), maltose binding protein (MBP), or glutathione-S-transferase (GST) tag.

In some embodiments, the PepCon further comprises a secretory signal peptide. In some embodiments, the secretory signal peptide is a prokaryotic secretory signal peptide. In some embodiments, the prokaryotic secretory signal peptide is a Lpp, LamB, LTB, MalE, OmpA, OmpC, OmpF, OmpT, PelB, PhoA, PhoE, or SpA peptide.

In some embodiments, the cleavage site is a protease cleavage site. In some embodiments, the protease cleavage site is an aminopeptidase M, bromelain, carboxypeptidase A, carboxypeptidase B, carboxypeptidase P, carboxypeptidase Y, cathepsin C, chymotrypsin, collagenase, dispase, elastase, endoproteinase Arg-C, endoproteinase Asp-N, endoproteinase Glu-C, endoproteinase Lys-C, enterokinase, factor Xa, ficin, human rhinovirus (HRV) 3C protease (or its GST fusion, PreScission protease), kallikrein, papain, pepsin, plasmin, pronase, proteinase K, subtilisin, TEV, thermolysin, thrombin, or trypsin cleavage site. In some embodiments, upon digestion at the protease cleavage site, the PepCon generates the two or more copies of the peptide.

In some embodiments, the PepCon comprises two or more copies of a single peptide. In some embodiments, the single peptide is a non-natural peptide. In some embodiments, the non-natural peptide is optimized for protein solubility or electrospray ionization ("ESI"). In some embodiments, the non-natural peptide comprises the sequence set forth in SEQ ID NO. 7 or a variant thereof which is at least 80% homologous to SEQ ID NO. 7. In some embodiments, the PepCon comprises 15 or more copies of the single peptide. In some embodiments, the PepCon comprises 30 or more copies of the single peptide.

DETAILED DESCRIPTION

Figure 1A:
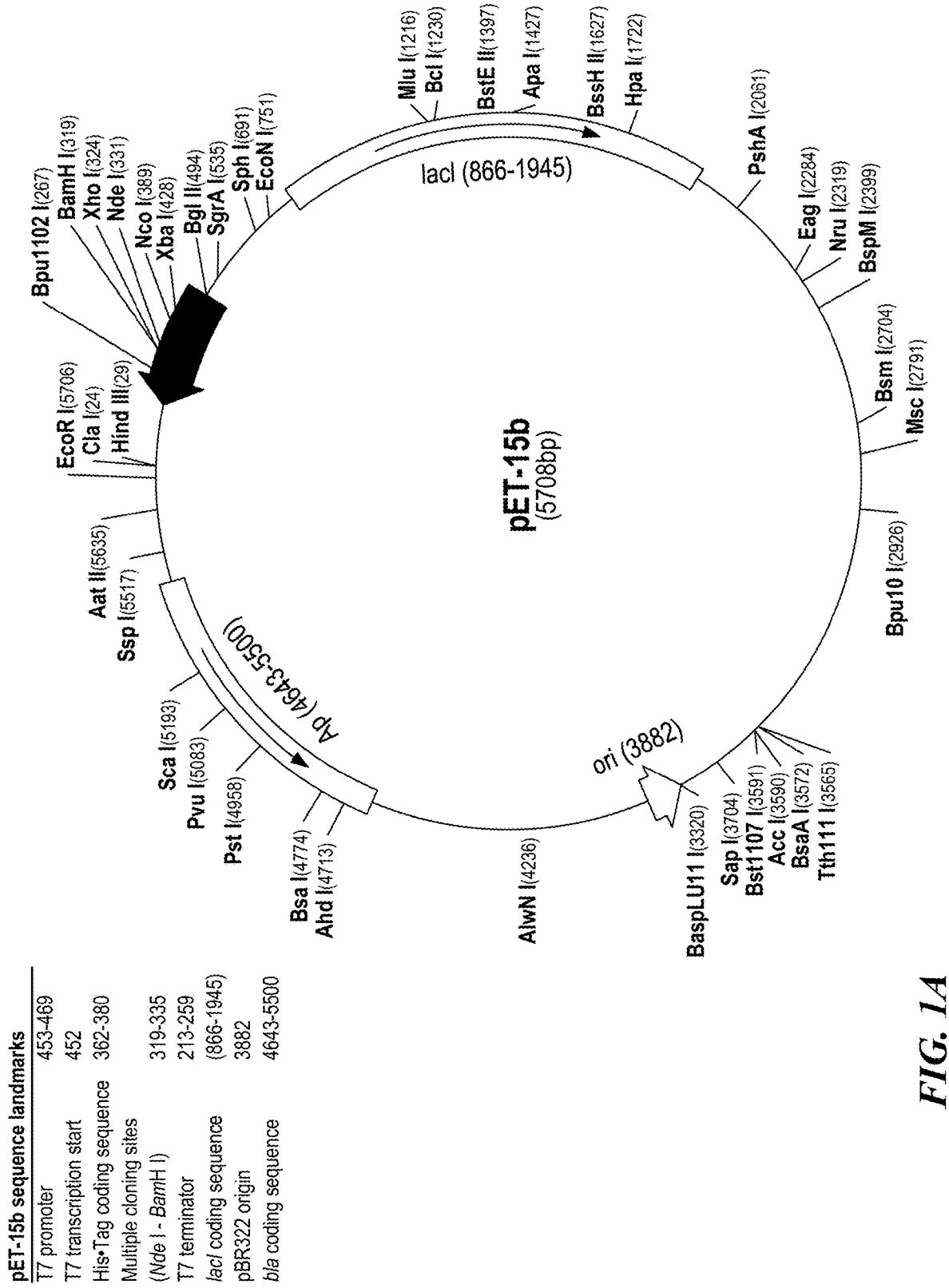
FIG. 1A shows a vector map of the pET-15b vector in accordance with one embodiment disclosed and described herein.

Described herein are peptide concatemers ("PepCons") optimized for use as proteomics standards. Unlike current approaches including QconCAT that utilize synthetic proteins composed of different peptides, the PepCon protein is a concatemeric protein that can be digested into multiple copies of the same peptide species. The presently disclosed technology is an improvement over the prior art because the prior art approaches do not involve concatenation of the same peptides. This improvement is not trivial given the challenges of (1) synthesizing highly-repetitive sequences of DNA, (2) expressing the protein in a manner that is not toxic to the cells, and (3) optimizing the sequence of the peptide for electrospray ionization mass spectrometry ("ESI MS") detection. Additionally, the PepCon described herein is optimized for protein solubility and ionization by ESI, which is the most common ion source for proteomics. Taken together, the PepCon protein can be spiked into a protein mixture at very low levels and digested and detected as single peptide species along with the analytes. Because of these unique features, the PepCon is suitable to be used as an internal, qualitative control for mass spectrometry.

Peptide Concatemer

In some embodiments, the PepCon of the present disclosure comprises two or more copies of a peptide linked by a cleavage site. In some embodiments, the PepCon further comprises an affinity tag. In other embodiments, the PepCon further comprises a secretory signal peptide.

Affinity Tag

In some embodiments, the PepCon of the present disclosure comprises an affinity tag. The PepCon protein is usually generated by in vivo or in vitro protein expression using a DNA template containing a nucleotide sequence that encodes the PepCon protein. Commonly used vectors for protein expression often contain a DNA sequence specifying an affinity tag for production of a tagged, recombinant protein, allowing easy purification of the protein product. When used in the presently described technology, the PepCon-encoding vector would produce a recombinant protein with an affinity tag fused to the PepCon, often at the N-terminus or C-terminus. The PepCon protein generated can thus be purified using the affinity tag. Non-limiting examples of an affinity tag include a FLAG, HA, His, myc, chitin binding protein (CBP), maltose binding protein (MBP), or glutathione-S-transferase (GST) tag. As shown in Example 1, the PepCon-encoding nucleotide sequence is cloned into the pET-15b vector, which has a DNA sequence for a string of six histidine (His) residues at the N-terminus (see FIG. 1B and SEQ ID NO. 3). The resulting PepCon protein has an N-terminal His tag (see SEQ ID NO. 4). As shown in Example 2, the PepCon-encoding nucleotide sequence is cloned into the pET-22b(+) vector, and the final PepCon protein has a His tag fused to its C-terminus (see FIG. 2B and SEQ ID NOs. 8, 10). His-tagged proteins can be purified by known immobilized metal affinity chromatography ("IMAC") protocols, taking advantage of the ability of His residues to bind metal ions (e.g., Ni, Co).

Secretory Signal Peptide

In some embodiments, the PepCon further comprises a secretory signal peptide, which can be particularly useful if the PepCon is generated by expression in a bacterial host cell (e.g., an E. coli cell). A secretory signal peptide not only increases the stability of the fused PepCon protein, it also allows the PepCon to be secreted out of the host cells, thereby enabling purification of the PepCon from cell supernatants and eliminating the need to lyse the cells for purification. Because host cells are usually bacterial cells (e.g., E. coli cells), the secretory signal peptide can be a prokaryotic secretory signal peptide. Non-limiting examples of a prokaryotic secretory signal peptide include a Lpp, LamB, LTB, MalE, OmpA, OmpC, OmpF, OmpT, PelB, PhoA, PhoE, and SpA peptide. For example, the pET-22b(+) vector carries an N-terminal PelB signal sequence for periplasmic localization of recombinant proteins (see FIG. 2B and SEQ ID NOs. 8, 16). When expressed using the pET-22b(+) vector, the PepCon protein is fused with the PelB signal sequence at its N-terminus, which facilitates secretion of the PepCon protein out of the host cells. The PelB signal sequence is cleaved by proteases during secretion.

Cleavage Site

In some embodiments, the two or more copies of a peptide contained in the PepCon protein are connected by a cleavage site. Cleavage at the cleavage sites allows the two or more copies of the peptide to be released from the PepCon protein. In some embodiments, the cleavage site is a protease cleavage site. Non-limiting examples of a cleavage site include an aminopeptidase M, bromelain, carboxypeptidase A, carboxypeptidase B, carboxypeptidase P, carboxypeptidase Y, cathepsin C, chymotrypsin, collagenase, dispase, elastase, endoproteinase Arg-C, endoproteinase Asp-N, endoproteinase Glu-C, endoproteinase Lys-C, enterokinase, factor Xa, ficin, human rhinovirus (HRV) 3C protease (or its GST fusion, PreScission protease), kallikrein, papain, pepsin, plasmin, pronase, proteinase K, subtilisin, TEV, thermolysin, thrombin, or trypsin cleavage site. In other embodiments, upon digestion by the protease at the cleavage site, the PepCon generates the two or more copies of the peptide. Therefore, although the PepCon is initially formed as a single protein, it can be digested into and behaves as peptide species for use during mass spectrometry.

Peptide

The PepCon comprises two or more copies of a peptide that are linked by a cleavage site. In some embodiments, the PepCon comprises two or more copies of a single peptide. Thus, upon digestion at the cleavage site, the PepCon protein turns into multiple copies of the same peptide and behaves as single peptide species for mass spectrometry.

In some embodiments, the single peptide is a non-natural peptide. This allows more flexibility in the design and optimization of the single peptide sequence. In some embodiments, the single peptide sequence is optimized for protein solubility. For example, Trevino et al., Amino acid contribution to protein solubility: Asp, Glu, and Ser contribute more favorably than the other hydrophilic amino acids in RNase Sa, *J. Mol. Biol.* (2007) 366(2):449-60, which is incorporated herein by reference, described a systematic approach to investigate the relative contributions of all 20 amino acids to protein solubility and found that aspartic acid, glutamic acid, and serine contributed most favorably to protein solubility, significantly more than other hydrophilic amino acids especially at high net charge. Thus, the findings of Trevino et al. can be utilized to design a single peptide that is high on aspartic acid, glutamic acid, or serine content to improve solubility of the peptide for subsequent uses including ESI and mass spectrometry processes.

In some embodiments, the single peptide sequence is optimized for ESI. Because ESI is the most common ion source for proteomics including protein mass spectrometry, optimization of the single peptide sequence contained in the PepCon for ESI improves peptide detection and consequently makes the PepCon a good internal standard for proteomics studies. For example, Nadler et al., MALDI versus ESI: The Impact of the Ion Source on Peptide Identification, *J. Proteome Res.* (2017) 16(3):1207-15, which is incorporated herein by reference, described efforts to investigate the influence of ion sources on peptide detection in large-scale proteomics applied either with ESI or with matrix-assisted laser desorption/ionization ("MALDI"). Nadler et al. found that leucine, alanine, and glutamic acid are among the amino acid composition of peptides most frequently identified by ESI- or MALDI-based mass spectrometry, and there was a position-correlated frequency within 5 amino acids of the N- or C-terminus of the identified peptides. Additionally, samples subject to mass spectrometry analysis are usually processed by trypsin digestion, and trypsin is a serine protease that selectively cleaves the peptide bond at the carboxyl side of an arginine or lysine residue. Thus, the C-terminal amino acid of peptides detected by mass spectrometry is usually arginine or lysine. Nadler et al. also found that with ESI-based mass spectrometry, the majority of peptides detected featured a lysine at the C-terminus, suggesting that lysine is preferred over arginine for ESI-optimization designs. Conversely, arginine is more frequently detected in MALDI-based mass spectrometry. Based on these findings, the single peptide contained in the PepCon can be optimized at individual amino acid positions to improve detection by ESI- or MALDI-based mass spectrometry.

In some embodiments, the non-natural peptide comprises the sequence set forth in SEQ ID NO. 7 or a variant thereof which is at least 80% homologous to SEQ ID NO. 7. Specifically, SEQ ID NO. 7 sets forth the amino acid sequence of "AAEEGELAAELAEK," which is optimized for both protein solubility and ESI according to the above illustrated principles.

In some embodiments, the PepCon comprises 5 or more copies, 10 or more copies, 15 or more copies, 20 or more copies, 25 or more copies, 30 or more copies, 35 or more copies, 40 or more copies, 45 or more copies, 50 or more copies of the single peptide. In Example 1 and Example 2, a peptide concatemer having 15 repeats of a single peptide sequence ("PepCon 15") is disclosed and described. In Example 3, a peptide concatemer having 30 repeats of a single peptide sequence ("PepCon 30") is disclosed and described.

In some embodiments, the PepCon according to the present disclosure, or any fragment thereof, is present in a composition.

In other embodiments, the PepCon has the sequence set forth in SEQ ID NO. 4 or SEQ ID NO. 10.

Methods for Generating a Peptide Concatemer

In some embodiments, the PepCon of the present disclosure can be generated by: (a) generating a vector comprising a nucleotide sequence encoding a PepCon, wherein the PepCon comprises two or more copies of a peptide linked by a cleavage site; and (b) expressing the PepCon from the nucleotide sequence. After a vector comprising the PepCon-encoding nucleotide sequence is generated, the PepCon can be expressed either by transforming a host cell (e.g., *E. coli*) or through an in vitro transcription/translation system (e.g., TNT®).

Vector Generation

As used herein, a "vector" may be any of a number of nucleic acids into which a desired sequence or sequences may be inserted, such as by restriction and ligation, for transport between different genetic environments or for expression in a host cell or a cell-free environment. Vectors are typically composed of DNA, although RNA vectors are also available. Vectors include, but are not limited to, DNA fragments, plasmids, fosmids, phagemids, virus genomes, and artificial chromosomes. Preferred vectors are those capable of autonomous replication and/or expression of the structural gene products present in the DNA segments to which they are operably joined.

Figure 2A:
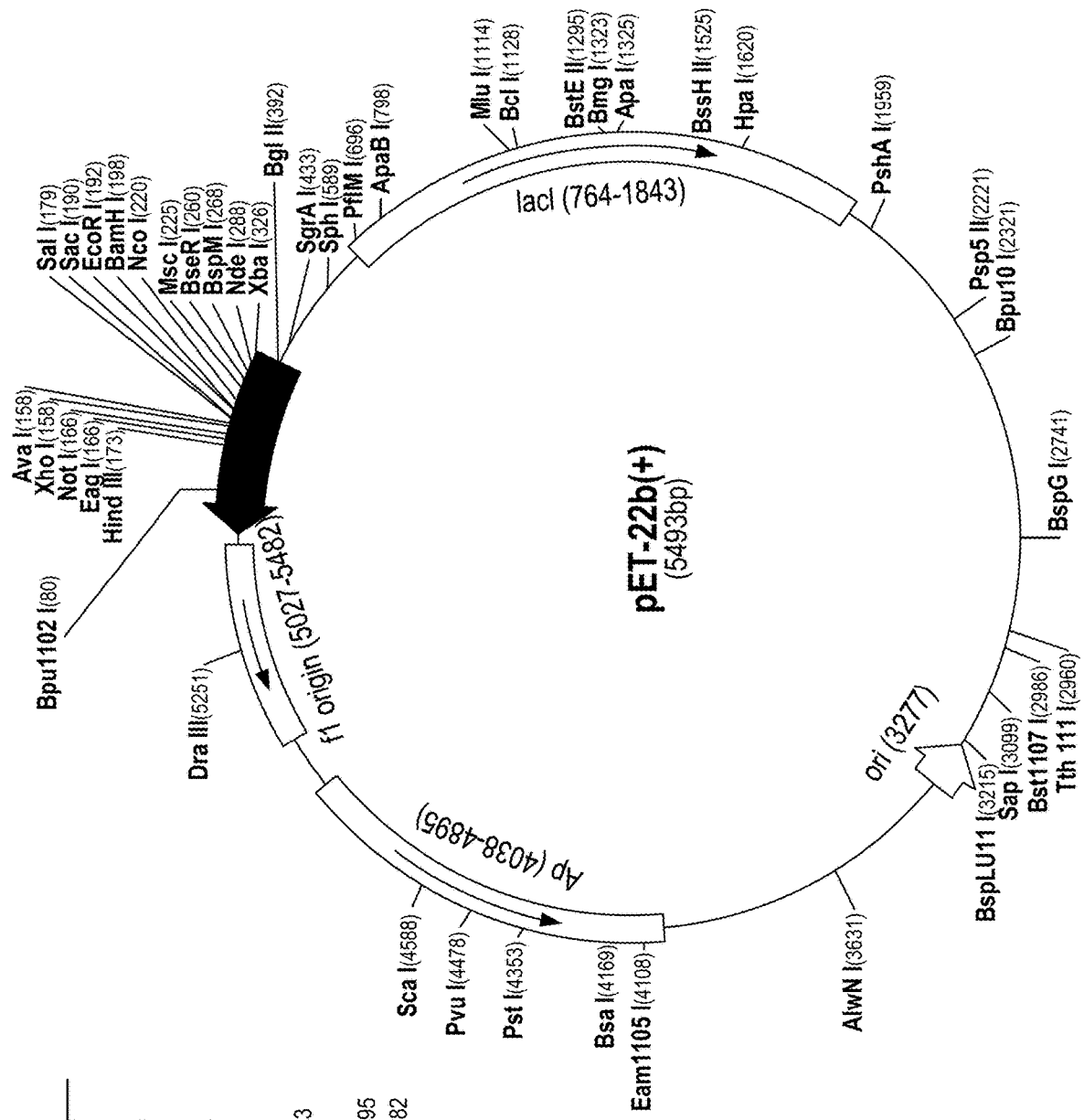
FIG. 2A shows a vector map of the pET-22b(+) vector in accordance with one embodiment disclosed and described herein.

A vector comprising a nucleotide sequence encoding the PepCon may be generated by standard cloning methods and techniques. Vectors containing all the necessary elements for gene expression and/or transformation of a host cell are commercially available and known to those skilled in the art. The elements necessary for gene expression in a host cell may include a promoter, an origin of replication, a ribosomal binding site, a start codon, a transcription termination sequence, a selectable marker, and a multiple cloning site. The multiple cloning site may contain multiple unique digestive enzyme sites, which can be used for cloning the nucleotide sequence encoding the PepCon. Both the pET-15b vector as discussed in Example 1 and the pET-22b(+) vector as discussed in Example 2 are examples of commercially available expression vectors (see FIGS. 1A, 2A). Vectors or plasmids suitable for in vitro transcription/translation usually contain a promoter, such as a T7 or a SP6 promoter, and nucleotide sequence encoding the desired protein.

In some embodiments, if expression of PepCon occurs in a host cell, the vector may also contain a secretory signal sequence for the generated recombinant protein to be secreted to the periplasmic space of the host cell. Non-limiting examples of a prokaryotic secretory signal peptide include a Lpp, LamB, LTB, MalE, OmpA, OmpC, OmpF, OmpT, PelB, PhoA, PhoE, or SpA peptide. For example, the pET-22b(+) vector carries an N-terminal PelB signal sequence to allow periplasmic localization of the generated protein (see FIG. 2B), which is then cleaved when the protein is secreted.

In some embodiments, whether in vivo or in vitro system is used for PepCon expression, the nucleotide sequence may additionally encode an affinity tag to allow purification of the generated recombinant PepCon protein. The presence of an affinity tag is also known to enhance the stability and solubility of the protein and the subsequent purification. Non-limiting examples of an affinity tag include a FLAG, HA, His, myc, chitin binding protein (CBP), maltose binding protein (MBP), or glutathione-S-transferase (GST) tag. For example, the cloning/expression region of the pET-15b vector contains a T7 promoter and an N-terminal His tag followed by a thrombin site and three unique cloning sites (e.g., BamHI, XhoI, and NdeI) (see FIG. 1B). Thus, the recombinant PepCon protein generated from the pET-15b construct would have an N-terminal His tag (see SEQ ID NO. 4). The pET-22b(+) vector has a C-terminal His tag sequence, enabling the generated protein to be C-terminally His-tagged (see FIG. 2B and SEQ ID NO. 10).

Expression

In some embodiments, the PepCon of the present disclosure can be generated by transforming a host cell (e.g., *E. coli*) with a vector comprising the PepCon-encoding nucleotide sequence. Using this approach, the PepCon is expressed in the host cell and can be subsequently purified from the cell lysates or cell supernatants. In other embodiments, the PepCon can be produced through an in vitro transcription/translation system (e.g., $T_NT$®), a convenient, cell-free process for protein expression.

After the nucleotide sequence encoding the PepCon is cloned into a vector, the orientation and sequence of the inserted nucleotide can be verified by digestion and sequencing. The resultant nucleotide-vector construct can be used to transform host cells by any of the known chemical or physical methods, such as the heat shock method. The transformed host cells are allowed to grow under optimal conditions, during which the encoded PepCons are expressed in the host cells. For subsequent use in protein mass spectrometry analysis, the PepCon protein can be expressed in host cells in the presence of media supplemented with isotope labeled amino acids. For protein collection, the host cells are harvested and lysed using any known method. If the PepCon is designed to be associated with a secretory signal peptide, the protein can be harvested from the culture media without the need to lyse the cells.

As an alternative to expression in host cells, in vitro transcription/translation systems (e.g., $T_NT$®) can be used to express PepCon from the encoding nucleotide sequence. In vitro transcription/translation systems provide a reaction mix containing all necessary components for coupled transcription/translations, including polymerases, nucleotides, salts, and amino acids, and thus enable cell-free protein expression in a convenient and efficient fashion. Plasmid DNA or PCR fragments containing an appropriate promotor and the PepCon-encoding nucleotide sequence are incubated with the reaction mix, usually for 60-90 minutes, for protein expression. The expressed proteins can be used directly after expression for other types of applications.

Purification

In some embodiments, the PepCon expressed by host cells or by in vitro transcription/translation systems are further purified before subsequent applications. An affinity tag present in the PepCon protein can facilitate the purification process. Purification of the generated PepCon protein using the affinity tag can be carried out by one of skill in the art using known biochemistry techniques, including affinity chromatography. Affinity chromatography is based on highly specific biological interactions between two molecules. Typically, one of the interacting molecules is solidified onto a matrix to create a stationary phase, and the other molecule is in the mobile phase. For example, proteins affixed with the His tag may be separated from a protein mixture by passing the protein mixture through a matrix column of immobilized metal ions, such as nickel or cobalt, due to the high affinity between the His tag and the metal ions.

Methods for Using a Peptide Concatemer

The PepCon of the present disclosure can be used as a qualitative control for protein mass spectrometry. In some embodiments, the method of using PepCons as a qualitative control for protein mass spectrometry comprises: (a) generating an analysis sample by combining a protein sample with a PepCon, wherein the PepCon comprises two or more copies of a peptide linked by a cleavage site; and (b) digesting the analysis sample with an agent capable of cleaving at the cleavage site. In other embodiments, the method of using the PepCon as a qualitative control for protein mass spectrometry further comprises analyzing the analysis sample by mass spectrometry.

Because the PepCon protein comprises multiple copies of the same peptide linked by a cleavage site, the PepCon protein can be spiked into a complex protein mixture at very low levels as an internal control for mass spectrometry analysis. Upon digestion of the protein mixture, the proteins to be analyzed break down to smaller fragments, and the PepCon protein "amplifies" into a detectable peptide species by breaking at the cleavage sites and releasing the multiple copies of the peptide. After digestion, the protein mixture is subject to mass spectrometry analysis, and the peptide species released from the PepCon would be detected as a peak on the chromatogram (see FIG. 5).

In summary, because the PepCon possesses the unique ability to amplify and produce detectable peptide species along with the proteins to be analyzed during mass spectrometry, it can serve as a good, non-obtrusive internal standard for protein mass spectrometry analysis.

EXAMPLES

Several aspects of the present technology described above are embodied in the following examples and associated description.

Example 1—PepCon 15 Encoded by the pET-15b Vector

A PepCon embodying the features described in the present disclosure is provided. This example shows a peptide concatemer having 15 repeats of a single peptide sequence ("PepCon 15"). Also described are methods of generating the PepCon 15 protein and using the PepCon 15 protein for mass spectrometry.

The amino acid sequence of PepCon 15 (SEQ ID NO. 1) comprises 15 repeats of a single peptide sequence "AAEEGELAAELAEK" (SEQ ID NO. 7), which is optimized for protein solubility and ESI according to principles disclosed in the present disclosure. Trypsin is frequently used in mass spectrometry-based proteomics to convert protein mixtures into more readily analyzable peptide populations, and it cleaves exclusively at the carboxyl side of an arginine or lysine residue. In view of this feature, the single peptide sequence is designed to end with a lysine residue, which can be cleaved by trypsin and readily recognized by ESI-based mass spectrometry.

To generate an expression vector for PepCon 15, the DNA sequence encoding PepCon 15 (SEQ ID NO. 2) was cloned into the XhoI and BamHI sites of the commercially available pET-15b vector, downstream of both the T7 promoter and the N-terminal His tag sequence (see FIG. 1B). pET-15b-PepCon 15 (SEQ ID NO. 3), the final expression vector construct containing the DNA sequence encoding PepCon 15, was then used to transform $E.\ coli$ cells, according to available laboratory techniques.

Expression of PepCon 15 was verified by Western blot. Briefly, BL21(DE3)pLysS, a widely used high-efficiency T7 expression $E.\ coli$ strain, was selected as the host for expression of PepCon 15. Overnight BL21(DE3)pLysS PepCon 15 cultures grown in Lbroth +100 µg/ml Ampicillin at 37° C. were diluted 1:100 into fresh media and grown for about 2-3 hours at 30° C. until OD600 reached about 0.4-0.6. Cultures were induced with 1 mM isopropyl β-D-1-thiogalactopyranoside ("IPTG") for protein expression, grown for an additional 12-16 hours at 30° C., and harvested by centrifugation at 7,000×g for 10 minutes. The supernatants were removed from the pellets, and the both supernatant and the pellets were frozen at −20° C. before analysis. For pellet samples, a 1.5 ml induced cell pellet was resuspended in 200 µl of 1×SDS sample buffer with βMe, boiled for 5 minutes at 95° C., sonicated for 10 minutes and re-boiled for 5 minutes at 95° C., prior to loading 20 µl onto a 4-20% TG SDS PA gel. For supernatant samples, supernatants were diluted 1:2 in 2×SDS sample buffer with βMe and boiled for 5 minutes at 95° C. prior to loading 20 µl onto a 4-20% TG SDS PA gel. Gels were run at 100-120 volts and then blotted onto a PVDF membrane using an iBLOT™ 2 (Thermo Fisher Scientific) cassette, blocked in Intercept® (LI-COR®) blocking buffer, and incubated overnight in anti-His antibody nutating at 4° C. Blots were washed in TPBS and incubated with IR680 or IR800 conjugated secondary antibodies rocking at room temperature for one hour, washed in TPBS and PBS, and then analyzed on an Odyssey® (LI-COR®) imaging system.

Figure 3:
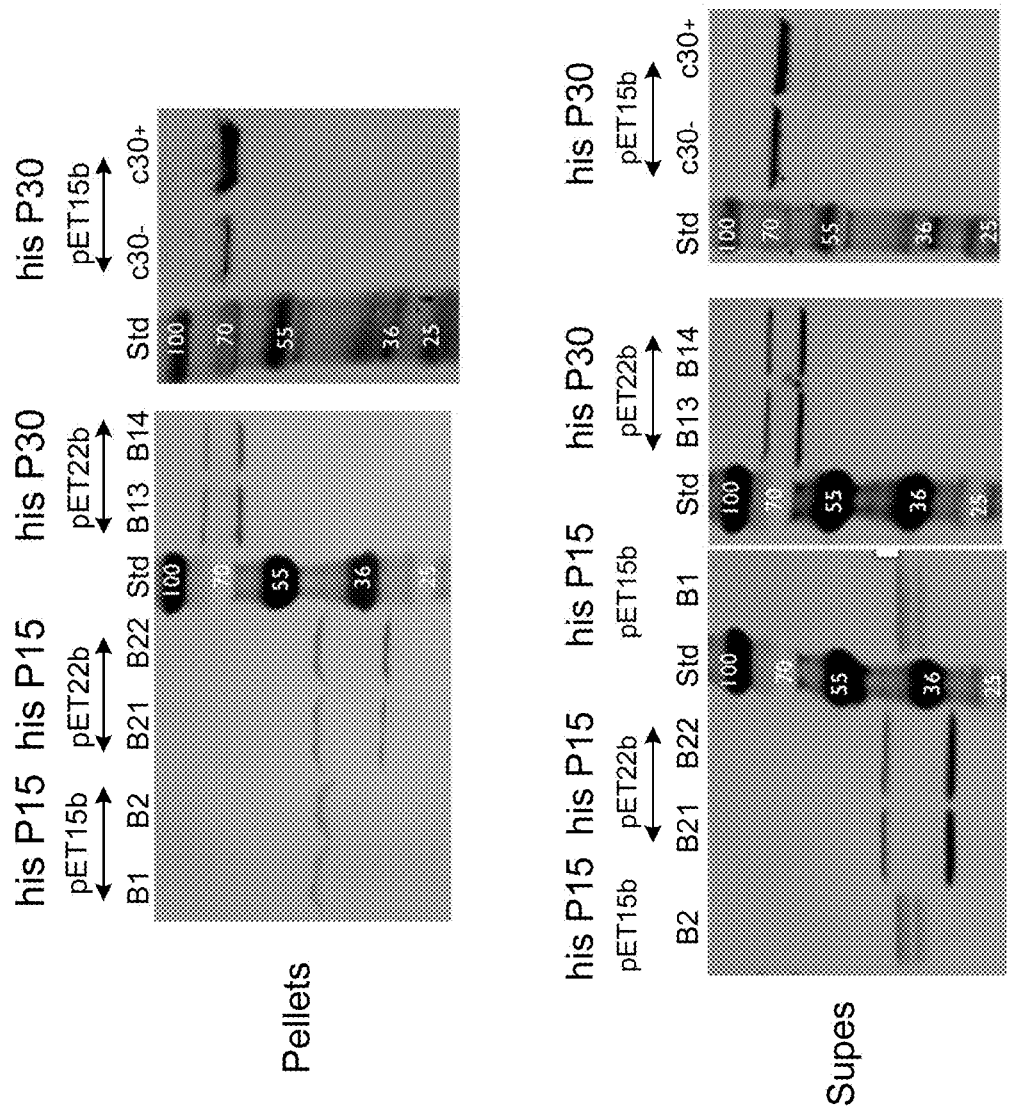
FIG. 3 shows expression of PepCon 15 and PepCon 30 from the pET-15b and pET-22b(+) vectors in E. coli by Western blot using anti-His antibody in accordance with one embodiment disclosed and described herein.

As shown in FIG. 3, Western blot results show expression of PepCon 15 encoded by pET-15b-PepCon 15 in $E.\ coli$ cells. The upper panels show Western blot results of the pellets; the bottom panels show Western blot results of the supernatants. As used in the present disclosure, "his P15" and "P15" are used interchangeably to indicate His-tagged PepCon 15, and "his P30" and "P30" are used interchangeably to indicate His-tagged PepCon 30. "pET15b" and "pET22b" are shorthand versions to indicate the vectors used for expression of the PepCon protein, i.e., pET-15b and pET-22b(+), respectively. "Std" indicates the protein standard for Western blot. "B1," "B2," "B13," "B14," "B21," "B22," c30" and the like indicate the particular $E.\ coli$ clones transformed with PepCon-encoding vectors. The "−" and "+" following the clone numbers, e.g., in "c30−" and "c30+," indicate the absence and presence, respectively, of protease inhibitors during expression.

As shown in FIG. 3, anti-His antibody was used to detect expression of His-tagged PepCon 15 from induced BL21 (DE3)pLysS cultures transformed with pET-15b-PepCon 15 (e.g., clones B1, B2), and a single major band correlating to PepCon 15 was detected in both the pellets and the supernatants from the induced BL21(DE3)pLysS cultures, confirming the expression of PepCon 15 from the pET-15b expression vector.

Expressed PepCon 15 was also purified from the supernatants of induced BL21(DE3)pLysS cultures using His SpinTrap™ TALON® (GE Healthcare), which is designed for purification of His-tagged proteins by immobilized metal affinity chromatography ("MAC"). BL21(DE3)pLysS induced culture supernatants expressing PepCon 15 were concentrated using Centriprep® Centrifugal Filter (Millipore) devices per manufacturer instructions, with 10 Kda molecular weight cutoff, to generate the load for His Spin-Trap™ TALON® (GE healthcare) columns. Proteins were purified as per manufacturer instructions except that additional elutions were added to ensure that the protein was removed from the columns to increase yield. Briefly, cell lysates containing His-tagged PepCon 15 were loaded into and mixed with prepared His SpinTrap™ TALON® columns to allow binding of His residues with resin-immobilized cobalt ions, and then washed with washing buffer. Next, His-tagged PepCon 15 was eluted with elution buffer and collected. All fractions were confirmed for protein content by analyzing on a 4-20% SDS PA gel. Positive elutions were combined and dialyzed overnight against PBS with two changes at 4° C., after which the resulting proteins were aliquoted, quick frozen in dry ice and ethanol bath, and stored at −80° C.

Figure 4:
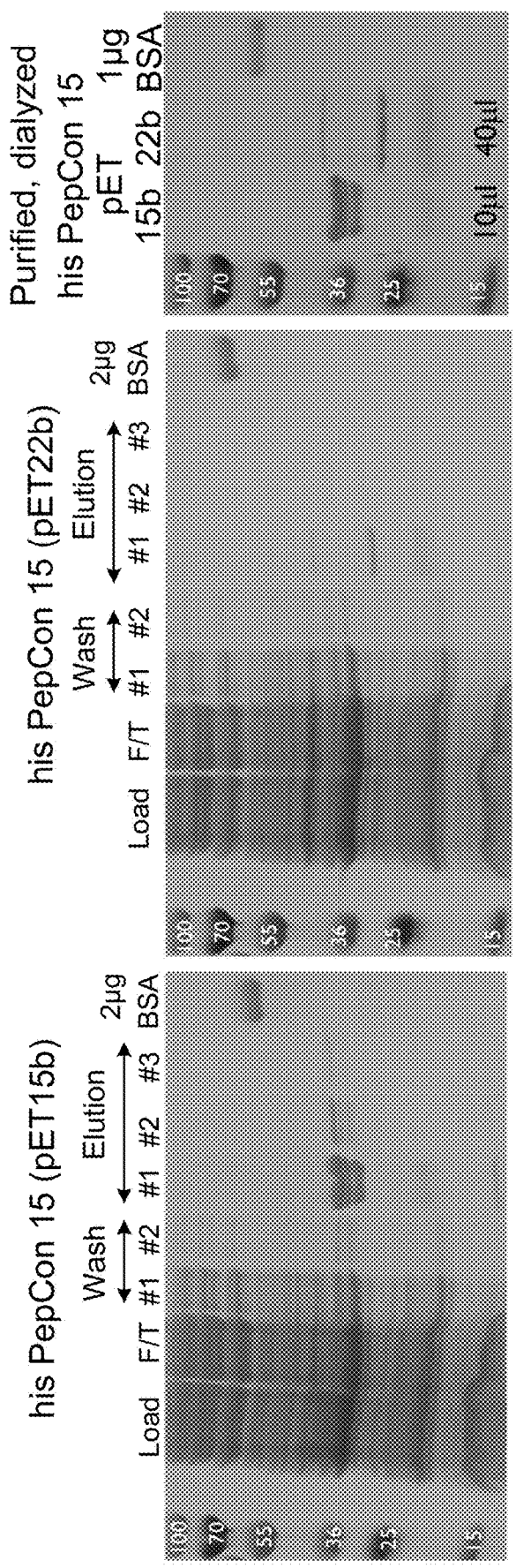
FIG. 4 shows purification of PepCon 15 expressed from the pET-15b and pET-22b(+) vectors from culture supernatants in accordance with one embodiment disclosed and described herein.

As shown in FIG. 4, left panel, load, flow-through (FT), wash, and elution fractions were separated by SDS-PAGE and stained, with 2 µg BSA run in parallel as control. Purified PepCon 15 appeared in the elution fractions at a greater intensity by comparison to the BSA standard, confirming effective purification of the PepCon 15 protein from induced supernatants. As shown in FIG. 4, right panel, 10 µl dialysis-purified PepCon 15 protein from the pET-15b expression vector was loaded and run on a gel with 1 µg BSA as control, and a major band corresponding to PepCon 15 was shown.

The final protein product has the amino acid sequence as shown in SEQ ID NO. 4. After trypsin cleavage at the lysine or arginine residue, the PepCon 15 protein was predicted to digest into 16 amino acid fragments, which are summarized at the table below.

TABLE 1

Peptide fragments from trypsin digestion of pET-15b-PepCon 15

| Fragment No. | Amino acid position | Peptide sequence |
| --- | --- | --- |
| 1 | 1-17 | MGSSHHHHHHSSGLVPR (SEQ ID NO. 5) |
| 2 | 18-37 | GSHMLEAAEEGELAAELAEK (SEQ ID NO. 6) |
| 3 | 38-51 | AAEEGELAAELAEK (SEQ ID NO. 7) |
| 4 | 52-65 | AAEEGELAAELAEK (SEQ ID NO. 7) |
| 5 | 66-79 | AAEEGELAAELAEK (SEQ ID NO. 7) |
| 6 | 80-93 | AAEEGELAAELAEK (SEQ ID NO. 7) |
| 7 | 94-107 | AAEEGELAAELAEK (SEQ ID NO. 7) |
| 8 | 108-121 | AAEEGELAAELAEK (SEQ ID NO. 7) |
| 9 | 122-135 | AAEEGELAAELAEK (SEQ ID NO. 7) |
| 10 | 136-149 | AAEEGELAAELAEK (SEQ ID NO. 7) |
| 11 | 150-163 | AAEEGELAAELAEK (SEQ ID NO. 7) |
| 12 | 164-177 | AAEEGELAAELAEK (SEQ ID NO. 7) |
| 13 | 178-191 | AAEEGELAAELAEK (SEQ ID NO. 7) |
| 14 | 192-205 | AAEEGELAAELAEK (SEQ ID NO. 7) |
| 15 | 206-219 | AAEEGELAAELAEK (SEQ ID NO. 7) |
| 16 | 220-233 | AAEEGELAAELAEK (SEQ ID NO. 7) |

The first fragment, amino acids 1 to 17 (SEQ ID NO. 5), mostly consists of the His tag. The second fragment, amino acids 18-37 (SEQ ID NO. 6) contains a few extra amino acids and the above described single peptide sequence (SEQ ID NO. 7). The other 14 fragments all consist of the single peptide sequence. Thus, in total, PepCon 15 should generate 15 copies of the single peptide sequence after trypsin treatment.

Figure 5:
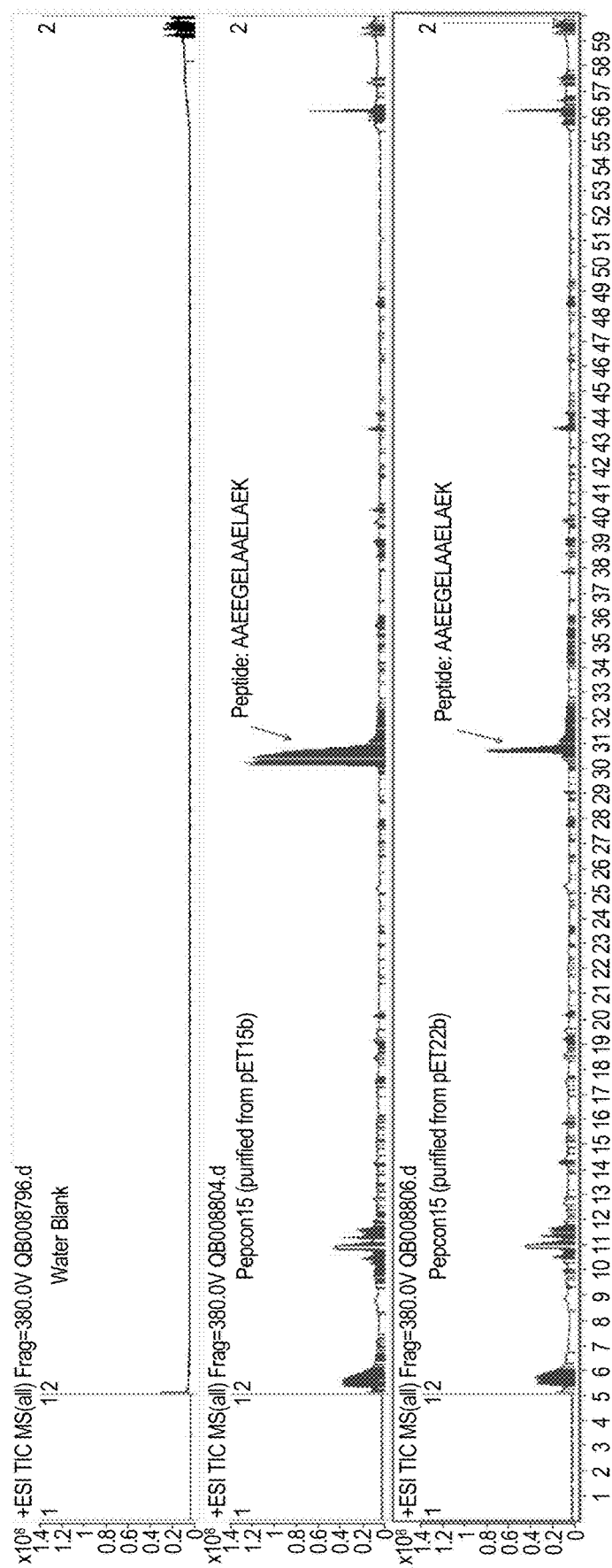
FIG. 5 is a total ion chromatogram showing the detection of the PepCon 15 single peptide after trypsin digestion in accordance with one embodiment disclosed and described herein.
Figure 6:
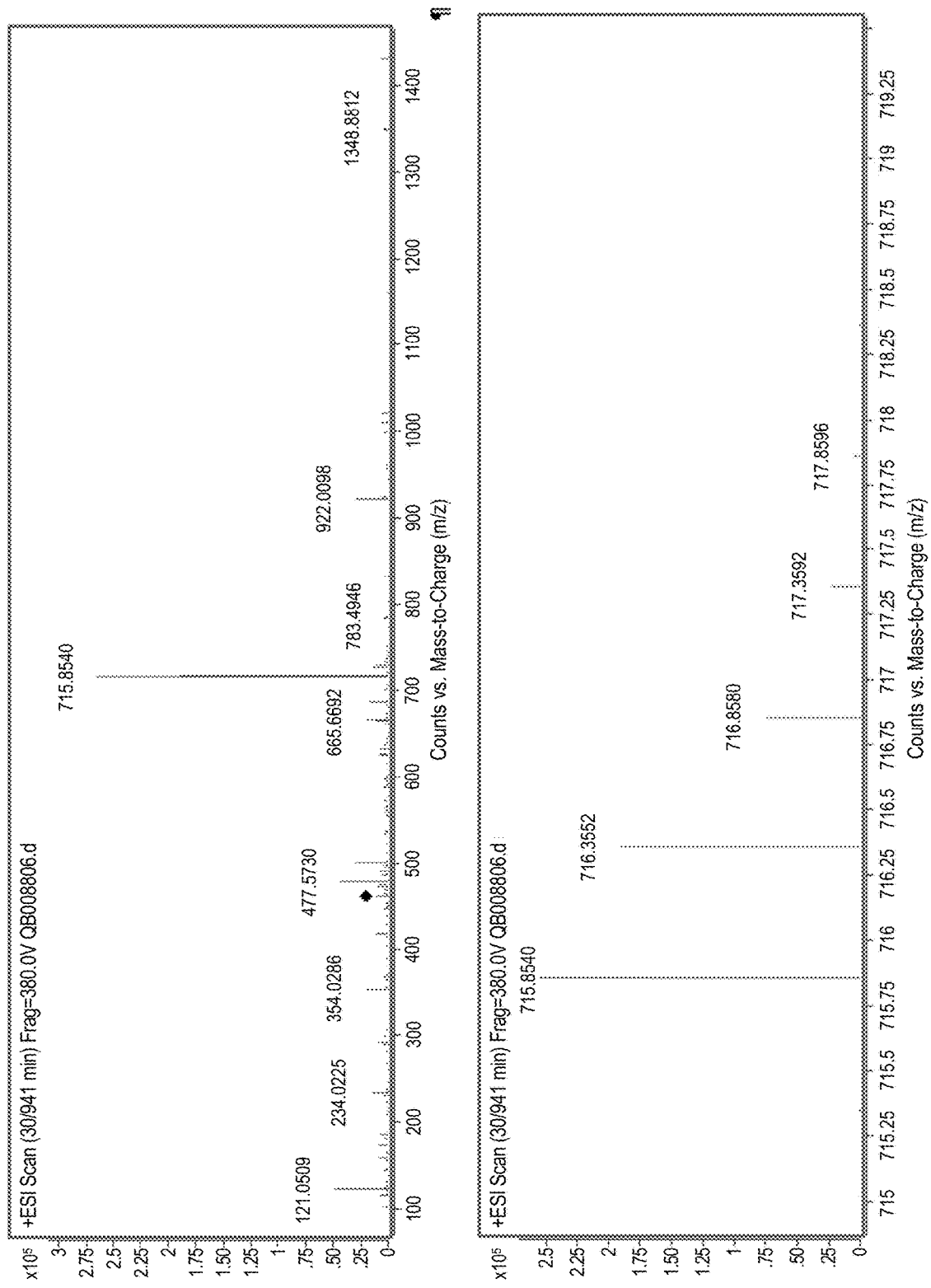
FIG. 6 shows the mass-to-charge ratio of the PepCon 15 single peptide after mass spectrometry analysis in accordance with one embodiment disclosed and described herein.

The ability of PepCon 15 to digest into single peptide species after trypsin treatment was confirmed by mass spectrometry data (see FIG. 5). Approximately 5 μg of purified His-tagged PepCon 15 protein were digested with trypsin as follows. Briefly, sample volumes were adjusted to 300 μl with ABC/Pmax buffer (50 mM ammonium bicarbonate ("ABC"), 0.01% Pmax), incubated with 50 mM DTT at room temperature for 20 minutes, heated to 95° C. for 10 minutes, heated at 37° C. for 60 minutes, incubated with 100 mM IAA at room temperature for 60 minutes in the dark, and finally incubated overnight nutating at room temperature with 150 μl containing 30 μg/ml Trpsin-TPCK in APC/Pmax buffer. The supernatant was transferred to a Millipore Ultra-free-MC-W Centrifugal filter (Durapore PVDF, 0.1 p.m), centrifuged for 5 minutes at 10,000×g, and the filtrate was aliquoted and frozen in an Agilent auto-sampler vial for mass spectrometry analysis. FIG. 5 shows the detection of a single major peak at the expected elution time for the peptide sequence, confirming the successful generation of the single peptide after digestion. Furthermore, mass spectrometry analysis showed that the single peptide species of PepCon 15 has a mass-to-charge (m/z) ratio of +2 (see FIG. 6). The predicted monoisotopic mass of the single peptide species is 1429.683. The measured mass is 1429.6924 ((715.8540−1.0078)×2).

Overall, these results show that PepCon 15 can be effectively generated by designing a corresponding nucleotide sequence, transfecting host cells with an expression vector containing the nucleotide sequence, and purifying the expressed protein from the cell lysates. Furthermore, mass spectrometry data confirms that PepCon 15 behaves as single peptide species after trypsin digestion, which makes PepCon 15 an ideal, non-intrusive control for mass spectrometry analysis in proteomics.

Example 2—PepCon 15 Encoded by the pET-22b(+) Vector

Figure 2B:
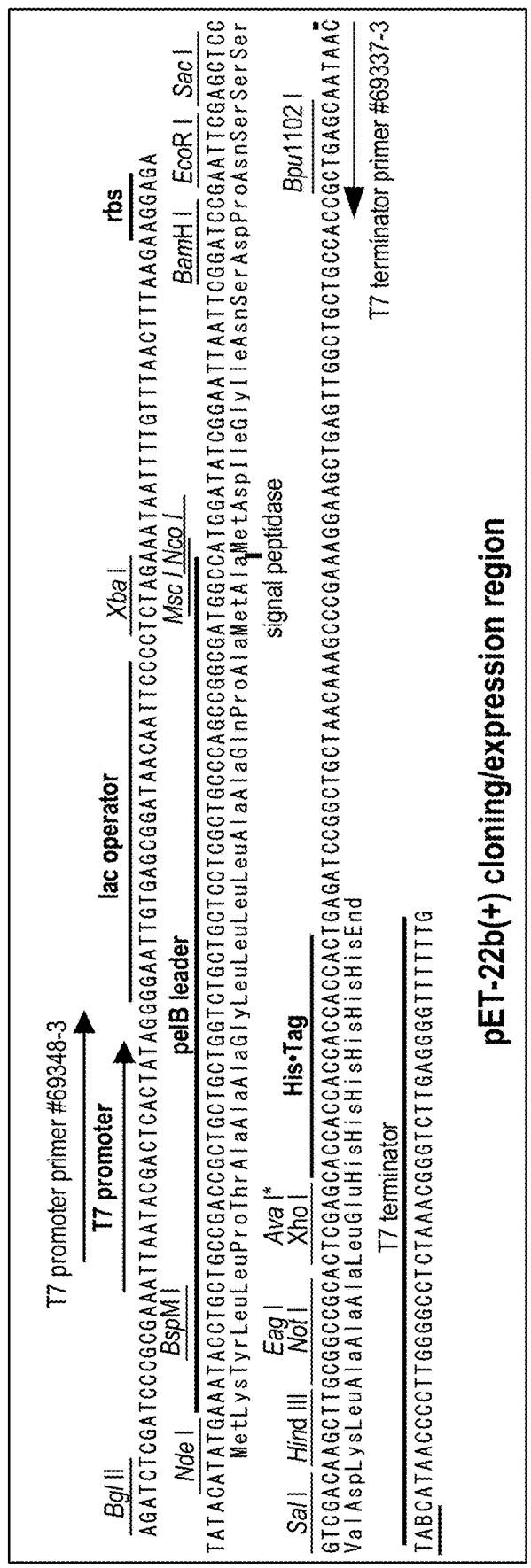
FIG. 2B shows the cloning/expression region of the pET-22b(+) vector in accordance with one embodiment disclosed and described herein.

Example 2 shows another approach to clone and generate PepCon 15, utilizing a different expression vector with different features. As shown in FIG. 2B, the DNA sequence encoding PepCon 15 (SEQ ID NO. 2) was cloned into the NcoI and XhoI sites of the pET-22b(+) vector, downstream of a PelB leader but upstream of a His tag sequence. PelB leader refers to the 22 N-terminal leader sequence of pectate lyase B of *Envinia carotovora* CE and has the amino acid sequence of "MKYLLPTAAAGLLLLAAQPAMA" (SEQ ID NO. 9). When attached to a protein, the PelB leader directs the protein to the bacterial periplasm, where the sequence is removed by a signal peptidase. The pET-22b(+)-PepCon 15 construct (SEQ ID NO. 8) was then used to transform *E. coli* cells. Because the PepCon 15 generated by the pET-22b(+) vector had a PelB signal sequence at its N-terminus, it was secreted out of the host cells when expressed, thereby eliminating the need to lyse the cells for protein collection. The PelB signal sequence was cleaved when entering the secretory pathway.

Expression of PepCon 15 from the pET-22b(+)-PepCon 15 construct was verified by Western blot using experimental protocols as discussed in Example 1. As shown in FIG. 3, Western blot results show expression of PepCon 15 from induced BL21(DE3)pLysS cultures transformed with the pET-22b(+)-PepCon 15 construct (e.g., clones B21, B22), in both the pellets and the supernatants. Anti-His antibody was used to detect His-tagged PepCon 15, and two bands were detected which possibly correlated to the PepCon 15 protein pre and post clipping of the PelB signal sequence that had been engineered into the construct. Therefore, PepCon 15 was also successfully expressed from the pET-22b(+) vector.

Expressed PepCon 15 protein was collected and purified from *E. coli* cell supernatants using the C-terminal His tag, according to the purification procedures disclosed and described in Example 1. FIG. 4, center panel, shows purification and quantification of PepCon 15 encoded by the pET-22b(+) vector. Load, flow-through (FT), wash, and elution fractions were separated by SDS-PAGE and stained, with 2 μg BSA run in parallel as control. As with the Western blot results, purified PepCon 15 appeared in the elution fractions as two bands, probably correlating to the two forms of PepCon15 with and without the PelB signal sequence. As shown in FIG. 4, right panel, 40 μl dialysis-purified PepCon 15 protein from the pET-22b(+)vector was load and run on a gel with 1 μg BSA as control, and again two bands corresponding to PepCon 15 with and without the signal sequence were visible. Thus, these data confirmed effective purification of the PepCon 15 protein from the pET-22b(+) vector as well.

The final protein product has the amino acid sequence as shown in SEQ ID NO. 10. The PepCon 15 protein was digested by trypsin into 16 amino acid fragments, which are summarized at the table below.

TABLE 2

Peptide fragments from trypsin digestion of pET-22b(+)-PepCon 15

| Fragment No. | Amino acid position | Peptide sequence |
|---|---|---|
| 1 | 1-16 | MDAAEEGELAAELAEK (SEQ ID NO. 11) |
| 2 | 17-30 | AAEEGELAAELAEK (SEQ ID NO. 7) |
| 3 | 31-44 | AAEEGELAAELAEK (SEQ ID NO. 7) |
| 4 | 45-58 | AAEEGELAAELAEK (SEQ ID NO. 7) |
| 5 | 59-72 | AAEEGELAAELAEK (SEQ ID NO. 7) |
| 6 | 73-86 | AAEEGELAAELAEK (SEQ ID NO. 7) |
| 7 | 87-100 | AAEEGELAAELAEK (SEQ ID NO. 7) |
| 8 | 101-114 | AAEEGELAAELAEK (SEQ ID NO. 7) |
| 9 | 115-128 | AAEEGELAAELAEK (SEQ ID NO. 7) |
| 10 | 129-142 | AAEEGELAAELAEK (SEQ ID NO. 7) |
| 11 | 143-156 | AAEEGELAAELAEK (SEQ ID NO. 7) |
| 12 | 157-170 | AAEEGELAAELAEK (SEQ ID NO. 7) |
| 13 | 171-184 | AAEEGELAAELAEK (SEQ ID NO. 7) |
| 14 | 185-198 | AAEEGELAAELAEK (SEQ ID NO. 7) |
| 15 | 199-212 | AAEEGELAAELAEK (SEQ ID NO. 7) |
| 16 | 213-220 | LEHHHHHH (SEQ ID NO. 12) |

The first fragment, amino acids 1 to 16 (SEQ ID NO. 11), consists of 2 extra amino acids and the single peptide sequence (SEQ ID NO. 7). Fragments 2-15 all consist of the single peptide sequence. Fragment 16 (SEQ ID NO. 12) mostly consists of the C-terminal His tag. Therefore, the PepCon 15 generated by pET-22b(+)-PepCon 15 was digested to 15 copies of the single peptide sequence upon trypsin treatment, which is confirmed by mass spectrometry data as shown in FIG. 5.

In summary, Examples 1 and 2 show successful design, generation, and purification of PepCon 15—a peptide concatemer having 15 repeats of a single peptide sequence—as verified by E. coli expression and mass spectrometry data. Consistent with the design, the final PepCon 15 protein can be effectively digested by trypsin at the lysine or arginine residue into 16 amino acid fragments, 15 of which are repeats of the peptide having the sequence of "AAEEGELAAELAEK" (SEQ ID NO. 7). Thus, PepCon 15 is a single protein that behaves as single peptide species after trypsin digestion, which makes PepCon 15 an ideal, non-intrusive control for mass spectrometry analysis in proteomics.

Example 3—PepCon 30 Encoded by the pET-15b and pET-22b(+) Vectors

Another example of a PepCon embodying the features described in the present disclosure is provided. In this example, the peptide concatemer, PepCon 30, has the amino acid sequence set forth in SEQ ID NO. 13. As the name suggests, PepCon 30 has 30 repeats of the single peptide sequence "AAEEGELAAELAEK" (SEQ ID NO. 7). The 30 single peptide sequences in PepCon 30 are connected by a trypsin cleavage site (i.e., a lysine residue), allowing PepCon 30 to amplify into 30 copies of the single peptide upon trypsin digestion.

Figure 1B:
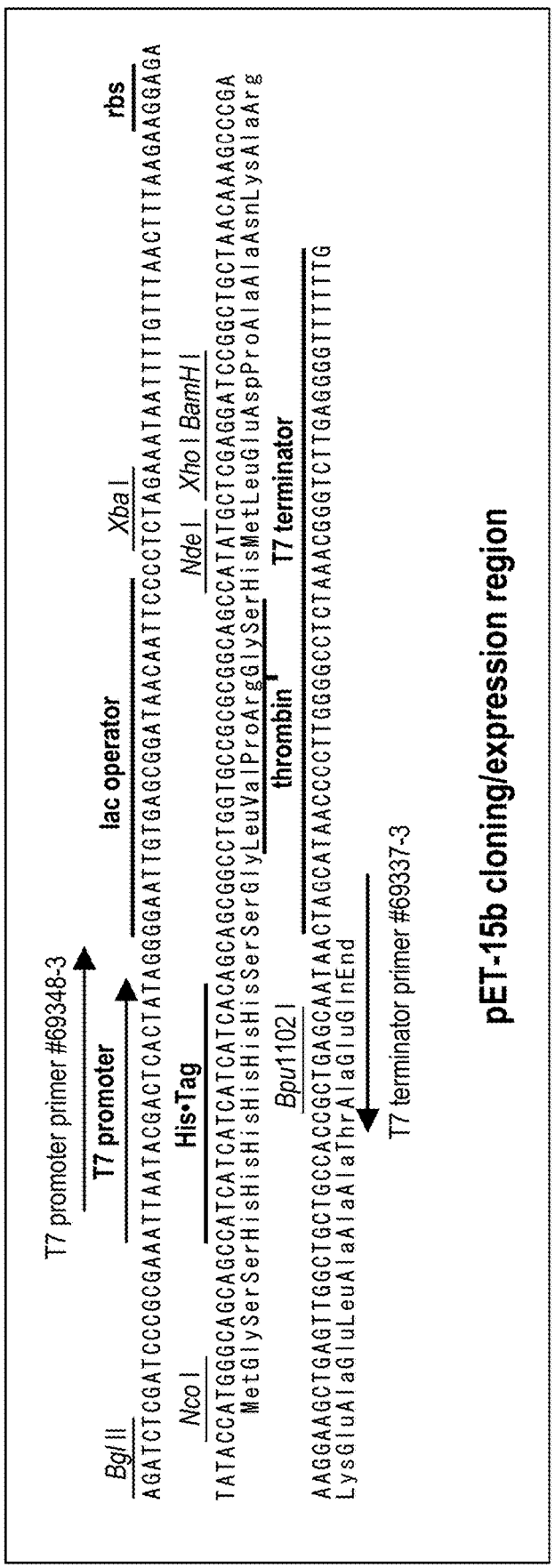
FIG. 1B shows the cloning/expression region of the pET-15b vector in accordance with one embodiment disclosed and described herein.

An N-terminally His-tagged PepCon protein 30 protein was generated in a manner similar to that utilized above for PepCon 15 design and construction. A DNA sequence encoding PepCon 30 (SEQ ID NO. 14) was cloned into the XhoI and BamHI sites of the pET-15b vector, downstream of the His tag sequence (FIG. 1B). The DNA sequence of the pET-15b-PepCon 30 construct is shown in SEQ ID NO. 15.

Similarly, to generate a secretory signal sequence-fused PepCon 30 protein, the DNA sequence encoding PepCon 30 (SEQ ID NO. 14) was cloned into the NcoI and XhoI sites of the pET-22b(+) vector, downstream of the PelB leader (see FIG. 2B). The pET-22b(+) vector also carries a His tag at the C-terminus. The DNA sequence of the pET-22b(+)-PepCon 30 construct is shown in SEQ ID NO. 16. The PelB signal sequence was cleaved when the expressed protein was secreted, resulting in a C-terminally His-tagged PepCon 30 protein.

Expression of PepCon 30 from both the pET-15b and the pET-22b(+) vectors was confirmed by Western blot using anti-His antibody using similar experimental protocols as discussed above (see FIG. 3). As shown in FIG. 3, expression of PepCon 30 from both the pET-15b and the pET-22b(+) vectors were detected in the pellets and the supernatants. Consistent with PepCon 15, a single major band for PepCon 30 from the pET-15b expression vector (e.g., clone c30) and two forms of the PepCon 30 from the pET-22b(+) expression vectors (e.g., clones B13, B14) were detected. It was observed that expression of PepCon 30 from the pET-15b vector cultured in the presence of protease inhibitors (e.g., c30+) was more robust compared to that cultured in the absence of protease inhibitors (e.g., c30−), suggesting that inhibition of proteases might result in reduced degradation of PepCon 30. The two forms of PepCon 30 from the pET-22b(+) vector may represent the pre and the post clipping of the signal sequence that had been engineered into the construct.

Purification, trypsin digestion, and mass spectrometry analysis of PepCon 30 expressed by either vector construct can be carried out according to similar techniques as disclosed and described herein. Like PepCon 15, PepCon 30 can also serve as non-intrusive standard in proteomic studies due to its ability to digest into single peptide species upon trypsin treatment.

Example 4—Confirmation of PepCon 15 and PepCon 30 Using Anti-PepCon Antibody

An antibody was generated to specifically recognize the single peptide contained within the PepCon proteins of Examples 1-3, i.e., "AAEEGELAAELAEK" (SEQ ID NO. 7). This antibody is useful for the detection, quantification, and characterization of PepCon proteins in a variety of assays such as Western blot, enzyme-linked immunosorbent assay ("ELISA"), immunohistochemistry, immunocytochemistry, flow cytometry, and immunoprecipitation.

The antibody specific to the PepCon peptide was generated using custom polyclonal antibody services offered by GenScript. Briefly, the PepCon peptide was synthesized and conjugated to proper carriers, followed by immunization of rabbits. After the third immunization, peptide antisera bleeds were screened against pure protein, as well as BL21(DE3) pLysS induced cultures expressing control plasmid or PepCon-expressing plasmids, to confirm positive Western reactivity. The rabbits were immunized a fourth time, after which the rabbits were euthanized, and the antiserum affinity was purified against the PepCon peptide. The affinity purified antibodies were tested by Western analysis on induced cultures expressing PepCon 15 and PepCon 30 and compared to Western blot results using the anti-His antibody.

Figure 7:
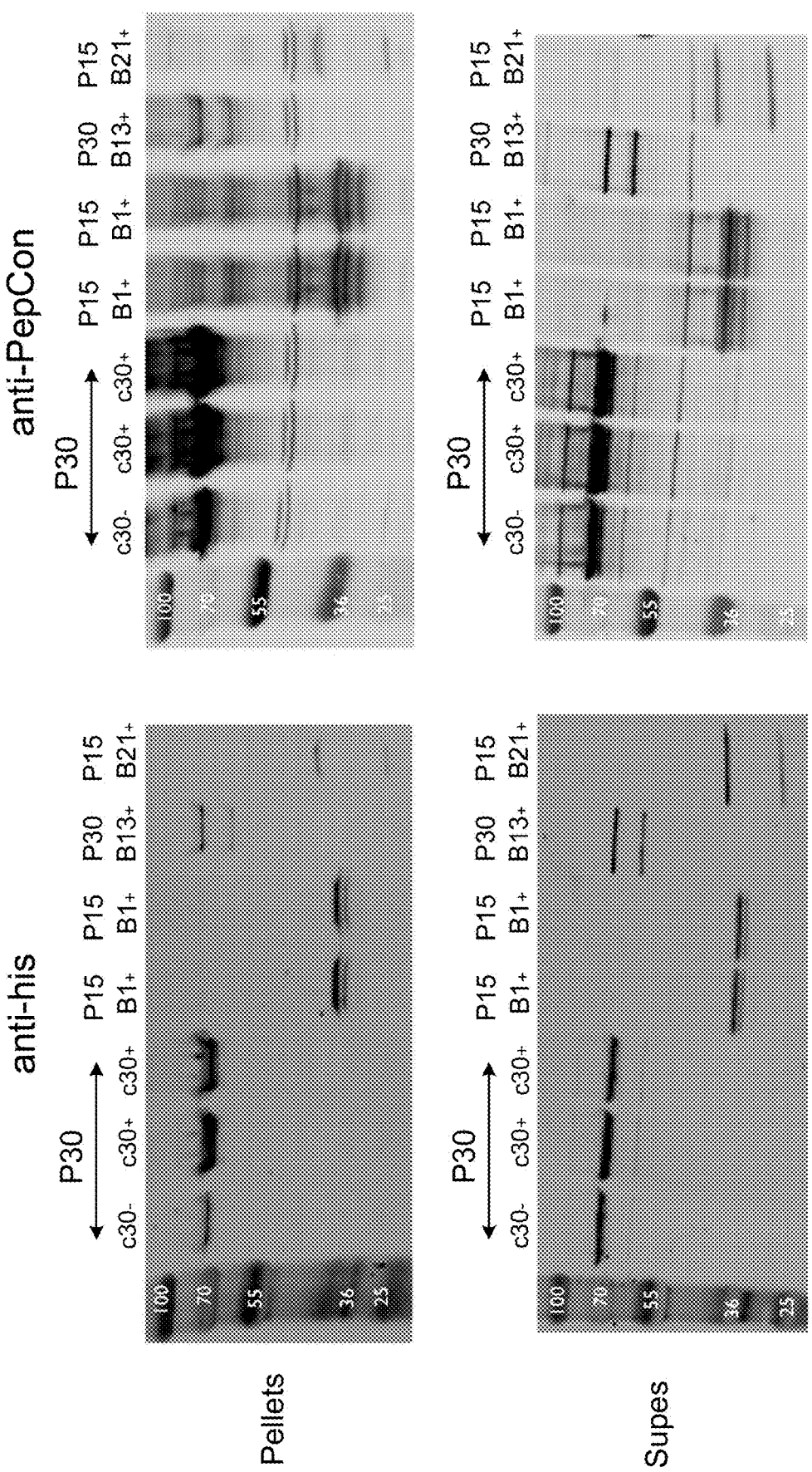
FIG. 7 shows detection of PepCon 15 and PepCon 30 expression in E. coli by Western blot using anti-His and anti-PepCon antibodies in accordance with one embodiment disclosed and described herein.

As shown in FIG. 7, the developed anti-PepCon antibody was effective at recognizing expressed PepCon 15 and PepCon 30 proteins. In the pellets and the supernatants derived from the various clones expressing PepCon 15 and PepCon 30, both the affinity purified anti-PepCon antibody and the anti-His antibody detected the expression of PepCon 15 and PepCon 30 proteins. The bands from the anti-PepCon antibody and the anti-His antibody appear to be the same, suggesting that both antibodies recognized the same protein. However, the anti-PepCon antibody exhibited stronger reactivity compared to the anti-His antibody. As with previously shown, a single major band for PepCon 15 and PepCon 30 from the pET-15b expression vector (e.g., B1 for PepCon 15, c30 for PepCon 30) was seen, and two forms from the pET-22b(+) expression vector (e.g., B21 for PepCon 15, B13 for PepCon 30) were seen.

Example 5—In Vitro Transcription/Translation of PepCon 15 and PepCon 30

In addition to in vivo expression using host E. coli cells, PepCon 15 and PepCon 30 described in Examples 1-3 were also expressed using in vitro transcription and translation reactions. In vitro transcription and translation using $^{PURExpress}$® (New England Bio Labs®, E3315Z) were performed off of plasmids encoding His-tagged PepCon 15 and PepCon 30 in both expression vectors, i.e., pET-15b and pET-22b(+). Briefly, 250 ng plasmid were combined with Solution A, amino acid mix, tRNA, factor mix, and 60 pmoles control ribosomes per manufacturer instructions and incubated at 30° C. overnight. Reactions were analyzed by SDS PAGE and Western analysis using affinity purified anti-PepCon antibody as described in Example 4. 1 ng His PepCon15 was loaded as a control for quantitative characterization.

Figure 8:
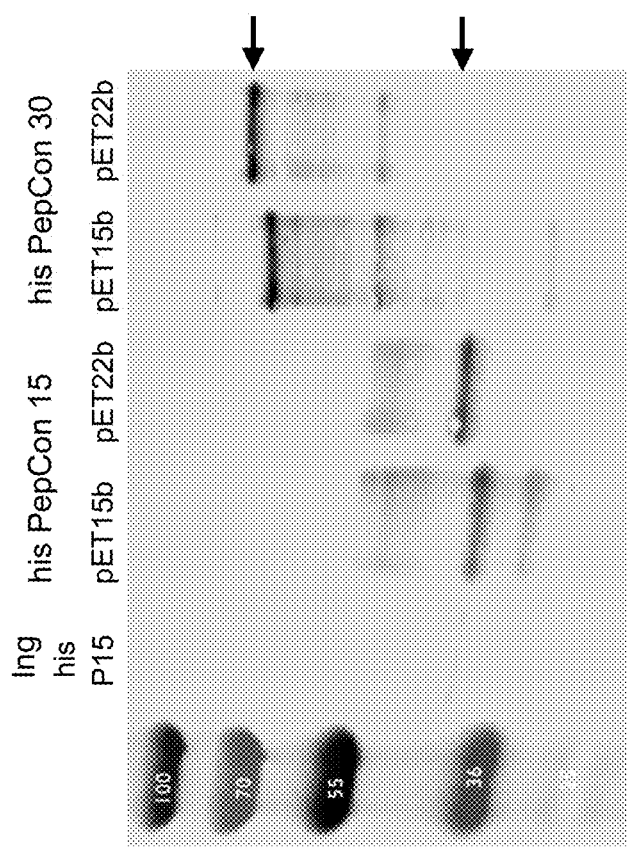
FIG. 8 shows detection of PepCon 15 and PepCon 30 expression through in vitro transcription/translation systems by Western blot using anti-PepCon antibody in accordance with one embodiment disclosed and described herein.

As shown in FIG. 8, in vitro expression of His-tagged PepCon 15 and PepCon 30 proteins from both the pET-15b and the pET-22b(+) vectors was detected using the affinity purified PepCon antibodies. As opposed to in vivo protein expression, only a single major band for PepCon 15 and PepCon 30 from either the pET-15b expression vector or the pET-22b(+) expression vector was seen, suggesting that the other form of lower molecular weight from the pET-22b(+) vector seen in the in vivo experiments is indeed a form of the PepCon protein wherein the signal sequence has been clipped off.

It is intended that the specification, together with the drawings, be considered exemplary only, where exemplary means an example. As used herein, the singular forms "a", "an" and "the" are intended to include the plural forms as well, unless the context clearly indicates otherwise. Additionally, the use of "or" is intended to include "and/or", unless the context clearly indicates otherwise.

While the present disclosure contains many specifics, these should not be construed as limitations on the scope of any invention or of what may be claimed, but rather as descriptions of features that may be specific to particular embodiments of particular inventions. Certain features that are described in this disclosure in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Moreover, the separation of various system components in the embodiments described in this disclosure should not be understood as requiring such separation in all embodiments.

Only a few implementations and examples are described, and other implementations, enhancements and variations can be made based on what is described and illustrated in this disclosure.

The invention claimed is:

1. A peptide concatemer ("PepCon") comprising two or more copies of a single, non-natural peptide linked by a cleavage site, wherein the peptide comprises the sequence set forth in SEQ ID NO. 7 or a variant thereof which is at least 80% homologous to SEQ ID NO. 7.

2. The PepCon of claim 1, further comprising an affinity tag.

3. The PepCon of claim 2, wherein the affinity tag is a FLAG, HA, His, myc, chitin binding protein (CBP), maltose binding protein (MBP), or glutathione-S-transferase (GST) tag.

4. The PepCon of claim 1, further comprising a secretory signal peptide.

5. The PepCon of claim 4, wherein the secretory signal peptide is a prokaryotic secretory signal peptide.

6. The PepCon of claim 5, wherein the prokaryotic secretory signal peptide is a Lpp, LamB, LTB, MalE, OmpA, OmpC, OmpF, OmpT, PelB, PhoA, PhoE, or SpA peptide.

7. The PepCon of claim 1, wherein the cleavage site is a protease cleavage site.

8. The PepCon of claim 7, wherein the protease cleavage site is an aminopeptidase M, bromelain, carboxypeptidase A, carboxypeptidase B, carboxypeptidase P, carboxypeptidase Y, cathepsin C, chymotrypsin, collagenase, dispase, elastase, endoproteinase Arg-C, endoproteinase Asp-N, endoproteinase Glu-C, endoproteinase Lys-C, enterokinase, factor Xa, ficin, human rhinovirus (HRV) 3C protease (or its GST fusion, PreScission protease), kallikrein, papain, pepsin, plasmin, pronase, proteinase K, subtilisin, TEV, thermolysin, thrombin, or trypsin cleavage site.

9. The PepCon of claim 7, wherein upon digestion at the protease cleavage site, the PepCon generates the two or more copies of the peptide.

10. The PepCon of claim 1, wherein the peptide is optimized for protein solubility or electrospray ionization ("ESI").

11. The PepCon of claim 1, wherein the PepCon comprises 15 or more copies of the single peptide.

12. The PepCon of claim 1, wherein the PepCon comprises 30 or more copies of the single peptide.

13. A peptide concatemer ("PepCon") having the sequence set forth in SEQ ID NO. 4 or SEQ ID NO. 10.

* * * * *

SEQUENCE LISTING

```
<160> NUMBER OF SEQ ID NOS: 16

<210> SEQ ID NO 1
<211> LENGTH: 210
<212> TYPE: PRT
<213> ORGANISM: Artificial Sequence
<220> FEATURE:
<223> OTHER INFORMATION: PepCon 15

<400> SEQUENCE: 1

Ala Ala Glu Glu Gly Glu Leu Ala Ala Glu Leu Ala Glu Lys Ala Ala
1               5                   10                  15

Glu Glu Gly Glu Leu Ala Ala Glu Leu Ala Glu Lys Ala Ala Glu Glu
            20                  25                  30

Gly Glu Leu Ala Ala Glu Leu Ala Glu Lys Ala Ala Glu Glu Gly Glu
        35                  40                  45

Leu Ala Ala Glu Leu Ala Glu Lys Ala Ala Glu Glu Gly Glu Leu Ala
    50                  55                  60
```

Ala Glu Leu Ala Glu Lys Ala Ala Glu Glu Gly Glu Leu Ala Ala Glu
65                  70                  75                  80

Leu Ala Glu Lys Ala Ala Glu Glu Gly Glu Leu Ala Ala Glu Leu Ala
                85                  90                  95

Glu Lys Ala Ala Glu Glu Gly Glu Leu Ala Ala Glu Leu Ala Glu Lys
            100                 105                 110

Ala Ala Glu Glu Gly Glu Leu Ala Ala Glu Leu Ala Glu Lys Ala Ala
        115                 120                 125

Glu Glu Gly Glu Leu Ala Ala Glu Leu Ala Glu Lys Ala Ala Glu Glu
    130                 135                 140

Gly Glu Leu Ala Ala Glu Leu Ala Glu Lys Ala Ala Glu Glu Gly Glu
145                 150                 155                 160

Leu Ala Ala Glu Leu Ala Glu Lys Ala Ala Glu Glu Gly Glu Leu Ala
                165                 170                 175

Ala Glu Leu Ala Glu Lys Ala Ala Glu Glu Gly Glu Leu Ala Ala Glu
            180                 185                 190

Leu Ala Glu Lys Ala Ala Glu Glu Gly Glu Leu Ala Ala Glu Leu Ala
        195                 200                 205

Glu Lys
    210

<210> SEQ ID NO 2
<211> LENGTH: 630
<212> TYPE: DNA
<213> ORGANISM: Artificial Sequence
<220> FEATURE:
<223> OTHER INFORMATION: PepCon 15

<400> SEQUENCE: 2
gcggcggagg aaggtgagct ggcggcggag ctggcggaaa aagcggcgga ggaaggcgaa         60
ctggcggctg agctggcgga aggctgctg aggaaggtg agctggcggc agagctggcg        120
gagaaagctg ctgaggaagg cgaactggcg gccgagctgg cggagaaggc cgctgaggaa       180
ggtgagctgg cggctgagct ggcggaaaaa gctgccgagg aaggcgaact ggcggcagag       240
ctggcggaaa aggctgccga ggaaggtgag ctggcggccg agctggcgga aaaagccgca       300
gaggaaggcg aactggcggc agagctggcg gaaaaagcag cagaggaagg tgagctggcg       360
gcagagctgg cggaaaaagc agcggaggaa ggcgaactgg cggcagagct ggcggaaaaa       420
gcagctgagg aaggtgagct ggcggcagag ctggcggaaa agcagccga ggaaggcgaa        480 ctggcggcag agctggcgga aaaagcagca gaggaaggtg agctggcggc agagctggcg       540
gaaaaagcag cagaggaagg cgagctggcg gcagagctgg cggaaaaagc agcagaggaa       600
ggtgagctgg cggcagagct ggcggaaaaa                                         630

<210> SEQ ID NO 3
<211> LENGTH: 6343
<212> TYPE: DNA
<213> ORGANISM: Artificial Sequence
<220> FEATURE:
<223> OTHER INFORMATION: pET-15b-PepCon 15

<400> SEQUENCE: 3
ttcttgaaga cgaaagggcc tcgtgatacg cctattttta taggttaatg tcatgataat         60
aatggtttct tagacgtcag gtggcacttt tcggggaaat gtgcgcggaa cccctatttg       120
tttatttttc taaatacatt caaatatgta tccgctcatg agacaataac cctgataaat       180
gcttcaataa tattgaaaaa ggaagagtat gagtattcaa catttccgtg tcgcccttat       240

```
tcccttttttt gcggcatttt gccttcctgt ttttgctcac ccagaaacgc tggtgaaagt      300
aaaagatgct gaagatcagt tgggtgcacg agtgggttac atcgaactgg atctcaacag      360
cggtaagatc cttgagagtt ttcgccccga agaacgtttt ccaatgatga gcacttttaa      420
agttctgcta tgtggcgcgg tattatcccg tgttgacgcc gggcaagagc aactcggtcg      480
ccgcatacac tattctcaga atgacttggt tgagtactca ccagtcacag aaaagcatct      540 tacgatggc atgacagtaa gagaattatg cagtgctgcc ataaccatga gtgataacac       600
tgcggccaac ttacttctga caacgatcgg aggaccgaag gagctaaccg cttttttgca      660
caacatgggg gatcatgtaa ctcgccttga tcgttgggaa ccggagctga atgaagccat      720
accaaacgac gagcgtgaca ccacgatgcc tgcagcaatg gcaacaacgt tgcgcaaact      780
attaactggc gaactactta ctctagcttc ccggcaacaa ttaatagact ggatggaggc      840
ggataaagtt gcaggaccac ttctgcgctc ggcccttccg gctggctggt ttattgctga      900
taaatctgga gccggtgagc gtgggtctcg cggtatcatt gcagcactgg ggccagatgg      960
taagccctcc cgtatcgtag ttatctacac gacggggagt caggcaacta tggatgaacg     1020
aaatagacag atcgctgaga taggtgcctc actgattaag cattggtaac tgtcagacca     1080
agtttactca tatatacttt agattgattt aaaacttcat ttttaattta aaaggatcta     1140
ggtgaagatc ctttttgata atctcatgac caaaatccct taacgtgagt tttcgttcca     1200
ctgagcgtca gaccccgtag aaaagatcaa aggatcttct tgagatcctt ttttttctgcg     1260 cgtaatctgc tgcttgcaaa caaaaaaacc accgctacca gcggtggttt gtttgccgga     1320
tcaagagcta ccaactcttt ttccgaaggt aactggcttc agcagagcgc agataccaaa     1380
tactgtcctt ctagtgtagc cgtagttagg ccaccacttc aagaactctg tagcaccgcc     1440 tacataccctc gctctgctaa tcctgttacc agtggctgct gccagtggcg ataagtcgtg     1500
tcttaccggg ttggactcaa gacgatagtt accggataag gcgcagcggt cgggctgaac     1560
ggggggttcg tgcacacagc ccagcttgga gcgaacgacc tacaccgaac tgagatacct     1620
acagcgtgag ctatgagaaa gcgccacgct tcccgaaggg agaaaggcgg acaggtatcc     1680
ggtaagcggc agggtcggaa caggagagcg cacgagggag cttccagggg gaaacgcctg     1740
gtatctttat agtcctgtcg ggtttcgcca cctctgactt gagcgtcgat ttttgtgatg     1800
ctcgtcaggg gggcggagcc tatggaaaaa cgccagcaac gcggcctttt tacgttcct      1860 ggccttttgc tggccttttg ctcacatgtt ctttcctgcg ttatccctg attctgtgga      1920 taaccgtatt accgcctttg agtgagctga taccgctcgc cgcagccgaa cgaccgagcg     1980
cagcgagtca gtgagcgagg aagcggaaga gcgcctgatg cggtattttc tccttacgca     2040
tctgtgcggt atttcacacc gcatatatgg tgcactctca gtacaatctg ctctgatgcc     2100
gcatagttaa gccagtatac actccgctat cgctacgtga ctgggtcatg gctgcgcccc     2160
gacacccgcc aacacccgct gacgcgccct gacgggcttg tctgctcccg gcatccgctt     2220
acagacaagc tgtgaccgtc tccgggagct gcatgtgtca gaggttttca ccgtcatcac     2280
cgaaacgcgc gaggcagctg cggtaaagct catcagcgtg gtcgtgaagc gattcacaga     2340
tgtctgcctg ttcatccgcg tccagctcgt tgagtttctc cagaagcgtt aatgtctggc     2400
ttctgataaa gcgggccatg ttaagggcgg ttttttcctg tttggtcact gatgcctccg     2460 tgtaagggg atttctgttc atgggggtaa tgataccgat gaaacgagag aggatgctca     2520
cgatacgggt tactgatgat gaacatgccc ggttactgga acgttgtgag ggtaaacaac     2580
```

```
tggcggtatg gatgcggcgg gaccagagaa aaatcactca gggtcaatgc cagcgcttcg    2640
ttaatacaga tgtaggtgtt ccacagggta gccagcagca tcctgcgatg cagatccgga    2700
acataatggt gcagggcgct gacttccgcg tttccagact ttacgaaaca cggaaaccga    2760
agaccattca tgttgttgct caggtcgcag acgttttgca gcagcagtcg cttcacgttc    2820
gctcgcgtat cggtgattca ttctgctaac cagtaaggca accccgccag cctagccggg    2880
tcctcaacga caggagcacg atcatgcgca cccgtggcca ggacccaacg ctgcccgaga    2940
tgcgccgcgt gcggctgctg gagatggcgg acgcgatgga tatgttctgc caagggttgg    3000
tttgcgcatt cacagttctc cgcaagaatt gattggctcc aattcttgga gtggtgaatc    3060
cgttagcgag gtgccgccgg cttccattca ggtcgaggtg gcccggctcc atgcaccgcg    3120
acgcaacgcg gggaggcaga caaggtatag ggcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga gaagaatcat    3360
aatggggaag gccatccagc ctcgcgtcgc gaacgccagc aagacgtagc ccagcgcgtc    3420
ggccgccatg ccgcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg gttttttctt tcaccagtga cgggcaac agctgattgc    3900 ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagccagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggc acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttttccc    4740 gcgttttcgc agaaacgtgg ctggcctggt tcaccacgcg ggaaacggtc tgataagaga    4800
caccggcata ctctgcgaca tcgtataacg ttactggttt cacattcacc accctgaatt    4860
gactctcttc cgggcgctat catgccatac cgcgaaaggt tttgcgccat tcgatggtgt    4920
ccgggatctc gacgctctcc cttatgcgac tcctgcatta ggaagcagcc cagtagtagg    4980
```

```
ttgaggccgt tgagcaccgc cgccgcaagg aatggtgcat gcaaggagat ggcgcccaac    5040 agtccccgg  ccacgggcc  tgccaccata cccacgccga acaagcgct  catgagcccg    5100 aagtggcgag cccgatcttc cccatcggtg atgtcggcga tataggcgcc agcaaccgca    5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacagca gcggcctggt gccgcgcggc agccatatgc tcgaggcggc ggaggaaggt    5400
gagctggcgg cggagctggc ggaaaaagcg gcggaggaag gcgaactggc ggctgagctg    5460
gcggagaagg ctgctgagga aggtgagctg gcggcagagc tggcggagaa agctgctgag    5520
gaaggcgaac tggcggccga gctggcggag aaggccgctg aggaaggtga gctggcggct    5580
gagctggcgg aaaaagctgc cgaggaaggc gaactggcgg cagagctggc ggaaaaggct    5640
gccgaggaag gtgagctggc ggccgagctg gcggaaaaag ccgcagagga aggcgaactg    5700
gcggcagagc tggcggaaaa agcagcagag gaaggtgagc tggcggcaga gctggcggaa    5760
aaagcagcgg aggaaggcga actgcggca  gagctggcgg aaaaagcagc tgaggaaggt    5820
gagctggcgg cagagctggc ggaaaaagca gccgaggaag gcgaactggc ggcagagctg    5880
gcggaaaaag cagcagagga aggtgagctg gcggcagagc tggcggaaaa agcagcagag    5940
gaaggcgagc tggcggcaga gctggcggaa aaagcagcag aggaaggtga gctggcggca    6000
gagctggcgg aaaaataagg gatccggctg ctaacaaagc ccgaaaggaa gctgagttgg    6060
ctgctgccac cgctgagcaa taactagcat aaccccttgg ggcctctaaa cgggtcttga    6120 ggggttttt  gctgaaagga ggaactatat ccggatatcc gcaagaggc  ccggcagtac    6180 cggcataacc aagcctatgc ctacagcatc cagggtgacg gtgccgagga tgacgatgag    6240
cgcattgtta gatttcatac acggtgcctg actgcgttag caatttaact gtgataaact    6300
accgcattaa agcttatcga tgataagctg tcaaacatga gaa                     6343
```

<210> SEQ ID NO 4
<211> LENGTH: 233
<212> TYPE: PRT
<213> ORGANISM: Artificial Sequence
<220> FEATURE:
<223> OTHER INFORMATION: pET-15b-PepCon 15

<400> SEQUENCE: 4

```
Met Gly Ser Ser His His His His His His Ser Ser Gly Leu Val Pro
1               5                   10                  15

Arg Gly Ser His Met Leu Glu Ala Ala Glu Glu Gly Glu Leu Ala Ala
            20                  25                  30

Glu Leu Ala Glu Lys Ala Ala Glu Glu Gly Glu Leu Ala Ala Glu Leu
        35                  40                  45

Ala Glu Lys Ala Ala Glu Glu Gly Glu Leu Ala Ala Glu Leu Ala Glu
    50                  55                  60

Lys Ala Ala Glu Glu Gly Glu Leu Ala Ala Glu Leu Ala Glu Lys Ala
65                  70                  75                  80

Ala Glu Glu Gly Glu Leu Ala Ala Glu Leu Ala Glu Lys Ala Ala Glu
                85                  90                  95

Glu Gly Glu Leu Ala Ala Glu Leu Ala Glu Lys Ala Ala Glu Glu Gly
            100                 105                 110

Glu Leu Ala Ala Glu Leu Ala Glu Lys Ala Ala Glu Glu Gly Glu Leu
```

```
                        115                 120                 125
Ala Ala Glu Leu Ala Glu Lys Ala Glu Glu Gly Glu Leu Ala Ala
                130                 135                 140

Glu Leu Ala Glu Lys Ala Ala Glu Glu Gly Glu Leu Ala Ala Glu Leu
145                 150                 155                 160

Ala Glu Lys Ala Ala Glu Glu Gly Glu Leu Ala Ala Glu Leu Ala Glu
                165                 170                 175

Lys Ala Ala Glu Glu Gly Glu Leu Ala Ala Glu Leu Ala Glu Lys Ala
                180                 185                 190

Ala Glu Glu Gly Glu Leu Ala Ala Glu Leu Ala Glu Lys Ala Ala Glu
                195                 200                 205

Glu Gly Glu Leu Ala Ala Glu Leu Ala Glu Lys Ala Ala Glu Glu Gly
                210                 215                 220

Glu Leu Ala Ala Glu Leu Ala Glu Lys
225                 230

<210> SEQ ID NO 5
<211> LENGTH: 17
<212> TYPE: PRT
<213> ORGANISM: Artificial Sequence
<220> FEATURE:
<223> OTHER INFORMATION: pET-15b-PepCon 15

<400> SEQUENCE: 5

Met Gly Ser Ser His His His His His His Ser Ser Gly Leu Val Pro
1               5                   10                  15

Arg

<210> SEQ ID NO 6
<211> LENGTH: 20
<212> TYPE: PRT
<213> ORGANISM: Artificial Sequence
<220> FEATURE:
<223> OTHER INFORMATION: pET-15b-PepCon 15

<400> SEQUENCE: 6

Gly Ser His Met Leu Glu Ala Ala Glu Glu Gly Glu Leu Ala Ala Glu
1               5                   10                  15

Leu Ala Glu Lys
            20

<210> SEQ ID NO 7
<211> LENGTH: 14
<212> TYPE: PRT
<213> ORGANISM: Artificial Sequence
<220> FEATURE:
<223> OTHER INFORMATION: PepCon 15

<400> SEQUENCE: 7

Ala Ala Glu Glu Gly Glu Leu Ala Ala Glu Leu Ala Glu Lys
1               5                   10

<210> SEQ ID NO 8
<211> LENGTH: 6069
<212> TYPE: DNA
<213> ORGANISM: Artificial Sequence
<220> FEATURE:
<223> OTHER INFORMATION: pET-22b(+)-PepCon 15

<400> SEQUENCE: 8
tggcgaatgg gacgcgccct gtagcggcgc attaagcgcg gcgggtgtgg tggttacgcg     60
```

```
cagcgtgacc gctacacttg ccagcgccct agcgcccgct cctttcgctt tcttcccttc    120
ctttctcgcc acgttcgccg gctttccccg tcaagctcta aatcgggggc tcccttttagg   180 gttccgattt agtgctttac ggcacctcga ccccaaaaaa cttgattagg gtgatggttc    240
acgtagtggg ccatcgccct gatagacggt ttttcgccct ttgacgttgg agtccacgtt    300
ctttaatagt ggactcttgt tccaaactgg aacaacactc aaccctatct cggtctattc    360
ttttgattta tagggatttt tgccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
tccgctcatg agacaataac cctgataaat gcttcaataa tattgaaaaa ggaagagtat    600
gagtattcaa catttccgtg tcgcccttat tcccttttt  gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataaaac tgcggccaac ttacttctga acgatcgg     1020 aggaccgaag gagctaaccg cttttttgca caacatgggg gatcatgtaa ctcgccttga   1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct aacgtgagt  tttcgttcca ctgagcgtca gaccccgtag aaaagatcaa    1620
aggatcttct tgagatcctt ttttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacatacctc gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg gtttcgcca     2160 cctctgactt gagcgtcgat ttttgtgatg ctcgtcaggg gggcggagcc tatgaaaaa     2220 cgccagcaac gcggcctttt tacggttcct ggccttttgc tggccttttg ctcacatgtt    2280
ctttcctgcg ttatcccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
```

```
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atggggtaa    2880 tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg cgataatgg cctgcttctc gccgaaacgt ttggtggcgg    3360
gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagccaga    4140
cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga ataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg caacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attcaccacc    4740
ctgaattgac tctcttccgg cgctatcat gccataccgc gaaaggtttt gcgccattcg    4800
```

```
atggtgtccg ggatctcgac gctctcccett atgcgactcc tgcattagga agcagcccag    4860
tagtaggttg aggccgttga gcaccgccgc cgcaaggaat ggtgcatgca aggagatggc    4920
gcccaacagt cccccggcca cggggcctgc caccatacce acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact ataggggaat tgtgagcgga taacaattcc    5160
cctctagaaa taattttgtt taactttaag aaggagatat acatatgaaa tacctgctgc    5220
cgaccgctgc tgctggtctg ctgctcctcg ctgcccagcc ggcgatggcc atggatgcgg    5280
cggaggaagg tgagctggcg gcggagctgg cggaaaaagc ggcggaggaa ggcgaactgg    5340
cggctgagct ggcggagaag gctgctgagg aaggtgagct ggcggcagag ctggcggaga    5400
aagctgctga ggaaggcgaa ctggcggccg agctggcgga aaggccgct gaggaaggtg    5460 agctggcggc tgagctggcg gaaaagctg ccgaggaagg cgaactggcg gcagagctgg    5520
cggaaaaggc tgccgaggaa ggtgagctgg cggccgagct ggcggaaaaa gccgcagagg    5580
aaggcgaact ggcggcagag ctggcggaaa aagcagcaga ggaaggtgag ctggcggcag    5640
agctggcgga aaagcagcg gaggaaggcg aactggcggc agagctggcg gaaaaagcag    5700
ctgaggaagg tgagctggcg gcagagctgg cggaaaaagc agccgaggaa ggcgaactgg    5760
cggcagagct ggcggaaaaa gcagcagagg aaggtgagct ggcggcagag ctggcggaaa    5820
aagcagcaga ggaaggcgag ctggcggcag agctggcgga aaaagcagca gaggaaggtg    5880
agctggcggc agagctggcg gaaaaactcg agcaccacca ccaccaccac tgagatccgg    5940
ctgctaacaa agcccgaaag gaagctgagt tggctgctgc caccgctgag caataactag    6000 cataaccccect tggggcctct aaacgggtct tgagggtttt tttgctgaaa ggaggaacta    6060
tatccggat                                                            6069
```

<210> SEQ ID NO 9
<211> LENGTH: 22
<212> TYPE: PRT
<213> ORGANISM: Artificial Sequence
<220> FEATURE:
<223> OTHER INFORMATION: PelB

<400> SEQUENCE: 9

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 10
<211> LENGTH: 220
<212> TYPE: PRT
<213> ORGANISM: Artificial Sequence
<220> FEATURE:
<223> OTHER INFORMATION: pET-22b(+)-PepCon 15

<400> SEQUENCE: 10

Met Asp Ala Ala Glu Glu Gly Glu Leu Ala Ala Glu Leu Ala Glu Lys
1               5                   10                  15

Ala Ala Glu Glu Gly Glu Leu Ala Ala Glu Leu Ala Glu Lys Ala Ala
            20                  25                  30

Glu Glu Gly Glu Leu Ala Ala Glu Leu Ala Glu Lys Ala Ala Glu Glu
        35                  40                  45

```
Gly Glu Leu Ala Ala Glu Leu Ala Glu Lys Ala Ala Glu Glu Gly Glu
        50                  55                  60
Leu Ala Ala Glu Leu Ala Glu Lys Ala Ala Glu Glu Gly Glu Leu Ala
 65                  70                  75                  80
Ala Glu Leu Ala Glu Lys Ala Ala Glu Glu Gly Glu Leu Ala Ala Glu
                 85                  90                  95
Leu Ala Glu Lys Ala Ala Glu Glu Gly Glu Leu Ala Ala Glu Leu Ala
            100                 105                 110
Glu Lys Ala Ala Glu Glu Gly Glu Leu Ala Ala Glu Leu Ala Glu Lys
        115                 120                 125
Ala Ala Glu Glu Gly Glu Leu Ala Ala Glu Leu Ala Glu Lys Ala Ala
    130                 135                 140
Glu Glu Gly Glu Leu Ala Ala Glu Leu Ala Glu Lys Ala Ala Glu Glu
145                 150                 155                 160
Gly Glu Leu Ala Ala Glu Leu Ala Glu Lys Ala Ala Glu Glu Gly Glu
                165                 170                 175
Leu Ala Ala Glu Leu Ala Glu Lys Ala Ala Glu Glu Gly Glu Leu Ala
            180                 185                 190
Ala Glu Leu Ala Glu Lys Ala Ala Glu Glu Gly Glu Leu Ala Ala Glu
        195                 200                 205
Leu Ala Glu Lys Leu Glu His His His His His His
    210                 215                 220

<210> SEQ ID NO 11
<211> LENGTH: 16
<212> TYPE: PRT
<213> ORGANISM: Artificial Sequence
<220> FEATURE:
<223> OTHER INFORMATION: pET-22b(+)-PepCon 15

<400> SEQUENCE: 11

Met Asp Ala Ala Glu Glu Gly Glu Leu Ala Ala Glu Leu Ala Glu Lys
1               5                   10                  15

<210> SEQ ID NO 12
<211> LENGTH: 8
<212> TYPE: PRT
<213> ORGANISM: Artificial Sequence
<220> FEATURE:
<223> OTHER INFORMATION: pET-22b(+)-PepCon 15

<400> SEQUENCE: 12

Leu Glu His His His His His His
1               5

<210> SEQ ID NO 13
<211> LENGTH: 420
<212> TYPE: PRT
<213> ORGANISM: Artificial Sequence
<220> FEATURE:
<223> OTHER INFORMATION: PepCon 30

<400> SEQUENCE: 13

Ala Ala Glu Glu Gly Glu Leu Ala Ala Glu Leu Ala Glu Lys Ala Ala
1               5                   10                  15
Glu Glu Gly Glu Leu Ala Ala Glu Leu Ala Glu Lys Ala Ala Glu Glu
            20                  25                  30
Gly Glu Leu Ala Ala Glu Leu Ala Glu Lys Ala Ala Glu Glu Gly Glu
        35                  40                  45
Leu Ala Ala Glu Leu Ala Glu Lys Ala Ala Glu Glu Gly Glu Leu Ala
```

```
            50                  55                  60
Ala Glu Leu Ala Glu Lys Ala Ala Glu Glu Gly Leu Ala Ala Glu
 65                  70                  75                  80

Leu Ala Glu Lys Ala Ala Glu Glu Gly Leu Ala Ala Glu Leu Ala
                 85                  90                  95

Glu Lys Ala Ala Glu Glu Gly Glu Leu Ala Ala Glu Leu Ala Glu Lys
            100                 105                 110

Ala Ala Glu Glu Gly Glu Leu Ala Ala Glu Leu Ala Glu Lys Ala Ala
            115                 120                 125

Glu Glu Gly Glu Leu Ala Ala Glu Leu Ala Glu Lys Ala Ala Glu Glu
            130                 135                 140

Gly Glu Leu Ala Ala Glu Leu Ala Glu Lys Ala Ala Glu Glu Gly Glu
145                 150                 155                 160

Leu Ala Ala Glu Leu Ala Glu Lys Ala Ala Glu Glu Gly Glu Leu Ala
                 165                 170                 175

Ala Glu Leu Ala Glu Lys Ala Ala Glu Glu Gly Glu Leu Ala Ala Glu
            180                 185                 190

Leu Ala Glu Lys Ala Ala Glu Glu Gly Glu Leu Ala Ala Glu Leu Ala
            195                 200                 205

Glu Lys Ala Ala Glu Glu Gly Glu Leu Ala Ala Glu Leu Ala Glu Lys
    210                 215                 220

Ala Ala Glu Glu Gly Glu Leu Ala Ala Glu Leu Ala Glu Lys Ala Ala
225                 230                 235                 240

Glu Glu Gly Glu Leu Ala Ala Glu Leu Ala Glu Lys Ala Ala Glu Glu
            245                 250                 255

Gly Glu Leu Ala Ala Glu Leu Ala Glu Lys Ala Ala Glu Glu Gly Glu
            260                 265                 270

Leu Ala Ala Glu Leu Ala Glu Lys Ala Ala Glu Glu Gly Glu Leu Ala
            275                 280                 285

Ala Glu Leu Ala Glu Lys Ala Ala Glu Glu Gly Glu Leu Ala Ala Glu
            290                 295                 300

Leu Ala Glu Lys Ala Ala Glu Glu Gly Glu Leu Ala Ala Glu Leu Ala
305                 310                 315                 320

Glu Lys Ala Ala Glu Glu Gly Glu Leu Ala Ala Glu Leu Ala Glu Lys
            325                 330                 335

Ala Ala Glu Glu Gly Glu Leu Ala Ala Glu Leu Ala Glu Lys Ala Ala
            340                 345                 350

Glu Glu Gly Glu Leu Ala Ala Glu Leu Ala Glu Lys Ala Ala Glu Glu
            355                 360                 365

Gly Glu Leu Ala Ala Glu Leu Ala Glu Lys Ala Ala Glu Glu Gly Glu
            370                 375                 380

Leu Ala Ala Glu Leu Ala Glu Lys Ala Ala Glu Glu Gly Glu Leu Ala
385                 390                 395                 400

Ala Glu Leu Ala Glu Lys Ala Ala Glu Glu Gly Glu Leu Ala Ala Glu
            405                 410                 415

Leu Ala Glu Lys
            420

<210> SEQ ID NO 14
<211> LENGTH: 1260
<212> TYPE: DNA
<213> ORGANISM: Artificial Sequence
<220> FEATURE:
<223> OTHER INFORMATION: PepCon 30
```

<400> SEQUENCE: 14

```
gcggcggagg aaggcgaact ggcggcggaa ctggcggaaa aagcggcgga agaaggtgaa      60
ctggcggcgg aactggcgga gaaggcggcg gaggaaggtg aattagctgc ggagttagct     120
gagaaagcgg cggaggaagg cgagctggcg gcggagctgg cggagaaggc ggcggaggaa     180
ggtgaacttg ctgcggagtt agccgaaaaa gctgctgagg aaggcgaatt agctgcggag     240
cttgctgaaa aggctgctga ggaaggtgaa ttagccgcgg agttagccga aaagctgct      300
gaggaaggcg agttagctgc ggagttagca gaaaaggctg ccgaggaagg tgaattagca     360
gcggagttag cagaaaaagc tgccgaggaa ggcgaattag ccgcggagct tgctgaaaaa     420
gctgcagagg aaggtgaatt agcggctgag ttagccgaaa aagccgctga ggaaggcgaa     480
cttgctgcgg agcttgctga aaggctgct gaggaaggtg aacttgccgc ggagttagca     540
gagaaagctg ccgaggaagg cgagttagcc gcggagttag cggaaaaagc tgcggaggaa     600
ggtgaactcg ctgcggagtt agcggagaaa gctgcagagg aaggcgaatt agcagcggag     660
cttgctgaga aagctgctga ggaaggtgaa ctagcggcgg agcttgccga aaaagccgcc     720
gaggaaggcg aacttgccgc ggagcttgcc gagaaggctg cggaggaagg tgaactggct     780
gctgagttag ccgagaaagc cgctgaggaa ggcgagcttg ctgcgagct tgccgagaaa     840
gctgcagagg aaggtgaact tgcagcggag cttgcagaaa agccgcaga ggaaggcgaa     900
cttgcagcgg agctcgctga aaaggccgct gaggaaggta actcgccgc ggagcttgca     960
gagaaagctg cggaggaagg cgaattagcg gcggagctgg cggaaaaggc cgccgaggaa    1020
ggtgaacttg cggctgagtt agcagaaaaa gccgcgagg aaggcgaatt ggctgctgag    1080
ctggcggaaa aggcagctga ggaaggtgaa ctggccgctg agttagcaga aaagccgcc     1140
gaggaaggcg agcttgccgc ggagcttgcg gaaaaagcag ccgaggaagg tgaactcgca    1200
gcggagcttg cggagaaagc tgcggaggaa ggcgagttag cagctgaact ggcggaaaag    1260
```

<210> SEQ ID NO 15
<211> LENGTH: 6969
<212> TYPE: DNA
<213> ORGANISM: Artificial Sequence
<220> FEATURE:
<223> OTHER INFORMATION: pET-15b-PepCon 30

<400> SEQUENCE: 15

```
ttcttgaaga cgaaagggcc tcgtgatacg cctattttta taggttaatg tcatgataat      60
aatggtttct tagacgtcag gtggcacttt tcggggaaat gtgcgcggaa cccctatttg     120
tttatttttc taaatacatt caaatatgta tccgctcatg agacaataac cctgataaat     180
gcttcaataa tattgaaaaa ggaagagtat gagtattcaa catttccgtg tcgcccttat     240
tcccttttt gcggcatttt gccttcctgt ttttgctcac ccagaaacgc tggtgaaagt     300
aaaagatgct gaagatcagt tgggtgcacg agtgggttac atcgaactgg atctcaacag     360
cggtaagatc cttgagagtt ttcgccccga agaacgtttt ccaatgatga gcacttttaa     420
agttctgcta tgtggcgcgg tattatcccg tgttgacgcc gggcaagagc aactcggtcg     480
ccgcatacac tattctcaga atgacttggt tgagtactca ccagtcacag aaaagcatct     540
tacggatggc atgacagtaa gagaattatg cagtgctgcc ataaccatga gtgataacac     600
tgcggccaac ttacttctga caacgatcgg aggaccgaag gagctaaccg cttttttgca     660
caacatgggg gatcatgtaa ctcgccttga tcgttgggaa ccggagctga atgaagccat     720
accaaacgac gagcgtgaca ccacgatgcc tgcagcaatg gcaacaacgt tgcgcaaact     780
```

```
attaactggc gaactactta ctctagcttc ccggcaacaa ttaatagact ggatggaggc      840
ggataaagtt gcaggaccac ttctgcgctc ggcccttccg gctggctggt ttattgctga      900
taaatctgga gccggtgagc gtgggtctcg cggtatcatt gcagcactgg ggccagatgg      960
taagccctcc cgtatcgtag ttatctacac gacggggagt caggcaacta tggatgaacg     1020
aaatagacag atcgctgaga taggtgcctc actgattaag cattggtaac tgtcagacca     1080
agtttactca tatatacttt agattgattt aaaacttcat ttttaattta aaaggatcta     1140
ggtgaagatc cttttttgata atctcatgac caaaatccct taacgtgagt tttcgttcca     1200
ctgagcgtca gaccccgtag aaaagatcaa aggatcttct tgagatcctt ttttttctgcg     1260 cgtaatctgc tgcttgcaaa caaaaaaacc accgctacca gcggtggttt gtttgccgga     1320
tcaagagcta ccaactcttt ttccgaaggt aactggcttc agcagagcgc agataccaaa     1380
tactgtcctt ctagtgtagc cgtagttagg ccaccacttc aagaactctg tagcaccgcc     1440
tacatacctc gctctgctaa tcctgttacc agtggctgct gccagtggcg ataagtcgtg     1500
tcttaccggg ttggactcaa gacgatagtt accggataag gcgcagcggt cgggctgaac     1560
ggggggttcg tgcacacagc ccagcttgga gcgaacgacc tacaccgaac tgagatacct     1620
acagcgtgag ctatgagaaa gcgccacgct tcccgaaggg agaaaggcgg acaggtatcc     1680
ggtaagcggc agggtcggaa caggagagcg cacgagggag cttccagggg gaaacgcctg     1740
gtatctttat agtcctgtcg ggtttcgcca cctctgactt gagcgtcgat ttttgtgatg     1800
ctcgtcaggg gggcggagcc tatggaaaaa cgccagcaac gcggcctttt tacggttcct     1860
ggccttttgc tggccttttg ctcacatgtt ctttcctgcg ttatccctg attctgtgga     1920 taaccgtatt accgcctttg agtgagctga taccgctcgc cgcagccgaa cgaccgagcg     1980
cagcgagtca gtgagcgagg aagcggaaga gcgcctgatg cggtattttc tccttacgca     2040
tctgtgcggt atttcacacc gcatatatgg tgcactctca gtacaatctg ctctgatgcc     2100
gcatagttaa gccagtatac actccgctat cgctacgtga ctgggtcatg gctgcgcccc     2160
gacacccgcc aacacccgct gacgcgccct gacgggcttg tctgctcccg gcatccgctt     2220
acagacaagc tgtgaccgtc tccgggagct gcatgtgtca ggttttca ccgtcatcac     2280 cgaaacgcgc gaggcagctg cggtaaagct catcagcgtg gtcgtgaagc gattcacaga     2340
tgtctgcctg ttcatccgcg tccagctcgt tgagtttctc cagaagcgtt aatgtctggc     2400
ttctgataaa gcgggccatg ttaagggcgg ttttttcctg tttggtcact gatgcctccg     2460
tgtaaggggg atttctgttc atgggggtaa tgataccgat gaaacgagag aggatgctca     2520
cgatacgggt tactgatgat gaacatgccc ggttactgga acgttgtgag ggtaaacaac     2580
tggcggtatg gatgcggcgg gaccagagaa aaatcactca gggtcaatgc cagcgcttcg     2640
ttaatacaga tgtaggtgtt ccacagggta gccagcagca tcctgcgatg cagatccgga     2700
acataatggt gcagggcgct gacttccgcg tttccagact ttacgaaaca cggaaaccga     2760
agaccattca tgttgttgct caggtcgcag acgttttgca gcagcagtcg cttcacgttc     2820
gctcgcgtat cggtgattca ttctgctaac cagtaaggca accccgccag cctagccggg     2880
tcctcaacga caggagcacg atcatgcgca cccgtggcca ggacccaacg ctgcccgaga     2940
tgcgccgcgt gcggctgctg gagatggcgg acgcgatgga tatgttctgc caagggttgg     3000
tttgcgcatt cacagttctc cgcaagaatt gattggctcc aattcttgga gtggtgaatc     3060
cgttagcgag gtgccgccgg cttccattca ggtcgaggtg gcccggctcc atgcaccgcg     3120
```

```
acgcaacgcg gggaggcaga caaggtatag ggcggcgcct acaatccatg ccaacccgtt    3180
ccatgtgctc gccgaggcgg cataaatcgc cgtgacgatc agcggtccag tgatcgaagt    3240
taggctggta agagccgcga gcgatccttg aagctgtccc tgatggtcgt catctacctg    3300
cctggacagc atggcctgca acgcgggcat cccgatgccg ccggaagcga agaatcat     3360
aatggggaag gccatccagc ctcgcgtcgc gaacgccagc aagacgtagc ccagcgcgtc    3420
ggccgccatg ccggcgataa tggcctgctt ctcgccgaaa cgtttggtgg cgggaccagt    3480
gacgaaggct tgagcgaggg cgtgcaagat tccgaatacc gcaagcgaca ggccgatcat    3540
cgtcgcgctc cagcgaaagc ggtcctcgcc gaaaatgacc cagagcgctg ccggcacctg    3600
tcctacgagt tgcatgataa agaagacagt cataagtgcg gcgacgatag tcatgccccg    3660
cgcccaccgg aaggagctga ctgggttgaa ggctctcaag ggcatcggtc gagatcccgg    3720
tgcctaatga gtgagctaac ttacattaat tgcgttgcgc tcactgcccg ctttccagtc    3780
gggaaacctg tcgtgccagc tgcattaatg aatcggccaa cgcgcgggga gaggcggttt    3840
gcgtattggg cgccagggtg ttttttcttt tcaccagtga gacgggcaac agctgattgc    3900
ccttcaccgc ctggccctga gagagttgca gcaagcggtc cacgctggtt tgccccagca    3960
ggcgaaaatc ctgtttgatg gtggttaacg gcgggatata acatgagctg tcttcggtat    4020
cgtcgtatcc cactaccgag atatccgcac caacgcgcag cccggactcg gtaatggcgc    4080
gcattgcgcc cagcgccatc tgatcgttgg caaccagcat cgcagtggga acgatgccct    4140
cattcagcat ttgcatggtt tgttgaaaac cggacatggc actccagtcg ccttcccgtt    4200
ccgctatcgg ctgaatttga ttgcgagtga gatatttatg ccagcagcc agacgcagac    4260
gcgccgagac agaacttaat gggcccgcta acagcgcgat ttgctggtga cccaatgcga    4320
ccagatgctc cacgcccagt cgcgtaccgt cttcatggga gaaaataata ctgttgatgg    4380
gtgtctggtc agagacatca agaaataacg ccggaacatt agtgcaggca gcttccacag    4440
caatggcatc ctggtcatcc agcggatagt taatgatcag cccactgacg cgttgcgcga    4500
gaagattgtg caccgccgct ttacaggctt cgacgccgct tcgttctacc atcgacacca    4560
ccacgctggg acccagttga tcggcgcgag atttaatcgc cgcgacaatt tgcgacggcg    4620
cgtgcagggc cagactggag gtggcaacgc caatcagcaa cgactgtttg cccgccagtt    4680
gttgtgccac gcggttggga atgtaattca gctccgccat cgccgcttcc acttttccc     4740
gcgttttcgc agaaacgtgg ctggcctggt tcaccacgcg ggaaacggtc tgataagaga    4800
caccggcata ctctgcgaca tcgtataacg ttactggttt cacattcacc ccctgaatt     4860
gactctcttc cgggcgctat catgccatac cgcgaaaggt tttgcgccat cgatggtgt     4920
ccgggatctc gacgctctcc cttatgcgac tcctgcatta ggaagcagcc cagtagtagg    4980
ttgaggccgt tgagcaccgc cgccgcaagg aatggtgcat gcaaggagat ggcgcccaac    5040
agtcccccgg ccacggggcc tgccaccata cccacgccga acaagcgct catgagcccg     5100
aagtggcgag cccgatcttc cccatcggtg atgtcggcga taggcgcc agcaaccgca     5160
cctgtggcgc cggtgatgcc ggccacgatg cgtccggcgt agaggatcga gatctcgatc    5220
ccgcgaaatt aatacgactc actatagggg aattgtgagc ggataacaat tcccctctag    5280
aaataatttt gtttaacttt aagaaggaga tataccatgg gcagcagcca tcatcatcat    5340
catcacagca gcggcctggt gccgcgcggc agccatatgc tcgaggcggc ggaggaaggc    5400
gaactggcgc cggaactggc ggaaaaagcg cggaagaag gtgaactggc ggcggaactg     5460
gcggagaagg cggcggagga aggtgaatta gctgcgagt tagctgagaa agcggcggag     5520
```

-continued

```
gaaggcgagc tggcggcgga gctggcggag aaggcggcgg aggaaggtga acttgctgcg   5580
gagttagccg aaaaagctgc tgaggaaggc gaattagctg cggagcttgc tgaaaaggct   5640
gctgaggaag gtgaattagc cgcggagtta ccgagaaaag ctgctgagga aggcgagtta   5700
gctgcggagt tagcagaaaa ggctgccgag gaaggtgaat tagcagcgga gttagcagaa   5760
aaagctgccg aggaaggcga attagccgcg gagcttgctg aaaaagctgc agaggaaggt   5820
gaattagcgg ctgagttagc cgaaaaagcc gctgaggaag cgaacttgc tgcggagctt   5880
gctgagaagg ctgctgagga aggtgaactt gccgcggagt tagcagagaa agctgccgag   5940
gaaggcgagt tagccgcgga gttagcgaaa aaagctgcgg aggaaggtga actcgctgcg   6000
gagttagcgg agaaagctgc agaggaaggc gaattagcag cggagcttgc tgagaaagct   6060
gctgaggaag gtgaactagc ggcggagctt gccgaaaaag ccgccgagga aggcgaactt   6120
gccgcggagc ttgccgagaa ggctgcggag gaaggtgaac tggctgctga gttagccgag   6180
aaagccgctg aggaaggcga gcttgctgcg gagcttgccg agaaagctgc agaggaaggt   6240
gaacttgcag cggagcttgc agaaaaagcc gcagaggaag gcgaacttgc agcggagctc   6300
gctgaaaagg ccgctgagga aggtgaactc gccgcggagc ttgcagagaa agctgcggag   6360
gaaggcgaat tagcggcgga gctggcggaa aaggccgccg aggaaggtga acttgcggct   6420
gagttagcag aaaaagccgc ggaggaaggc gaattggctg ctgagctggc ggaaaaggca   6480
gctgaggaag gtgaactggc cgctgagtta gcagagaaag ccgccgagga aggcgagctt   6540
gccgcggagc ttgcggaaaa agcagccgag gaaggtgaac tcgcagcgga gcttgcggag   6600
aaagctgcgg aggaaggcga gttagcagct gaactggcgg aaaagggatc cggctgctaa   6660
caaagcccga aaggaagctg agttggctgc tgccaccgct gagcaataac tagcataacc   6720
ccttggggcc tctaaacggg tcttgagggg ttttttgctg aaaggaggaa ctatatccgg   6780
atatcccgca agaggcccgg cagtaccggc ataaccaagc ctatgcctac agcatccagg   6840
gtgacggtgc cgaggatgac gatgagcgca ttgttagatt tcatacacgg tgcctgactg   6900
cgttagcaat ttaactgtga taaactaccg cattaaagct tatcgatgat aagctgtcaa   6960
acatgagaa                                                          6969
```

<210> SEQ ID NO 16
<211> LENGTH: 6699
<212> TYPE: DNA
<213> ORGANISM: Artificial Sequence
<220> FEATURE:
<223> OTHER INFORMATION: pET-22b(+)-PepCon 30

<400> SEQUENCE: 16

```
tggcgaatgg gacgcgccct gtagcggcgc attaagcgcg gcgggtgtgg tggttacgcg     60
cagcgtgacc gctacacttg ccagcgccct agcgcccgct cctttcgctt tcttcccttc    120
ctttctcgcc acgttcgccg gctttccccg tcaagctcta aatcggggc tccctttagg    180
gttccgattt agtgctttac ggcacctcga ccccaaaaaa cttgattagg gtgatggttc    240
acgtagtggg ccatcgccct gatagacggt ttttcgccct tgacgttgg agtccacgtt    300
ctttaatagt ggactcttgt tccaaactgg aacaacactc aaccctatct cggtctattc    360
ttttgattta agggatttt gccgatttc ggcctattgg ttaaaaaatg agctgattta    420
acaaaaattt aacgcgaatt ttaacaaaat attaacgttt acaatttcag gtggcacttt    480
tcggggaaat gtgcgcggaa cccctatttg tttatttttc taaatacatt caaatatgta    540
```

-continued

```
tccgctcatg agacaataac cctgataaat gcttcaataa tattgaaaaa ggaagagtat    600
gagtattcaa catttccgtg tcgcccttat tcccttttt gcggcatttt gccttcctgt    660
ttttgctcac ccagaaacgc tggtgaaagt aaaagatgct gaagatcagt tgggtgcacg    720
agtgggttac atcgaactgg atctcaacag cggtaagatc cttgagagtt ttcgccccga    780
agaacgtttt ccaatgatga gcacttttaa agttctgcta tgtggcgcgg tattatcccg    840
tattgacgcc gggcaagagc aactcggtcg ccgcatacac tattctcaga atgacttggt    900
tgagtactca ccagtcacag aaaagcatct tacggatggc atgacagtaa gagaattatg    960
cagtgctgcc ataaccatga gtgataacac tgcggccaac ttacttctga caacgatcgg   1020
aggaccgaag gagctaaccg cttttttgca acaacatgggg gatcatgtaa ctcgccttga   1080
tcgttgggaa ccgagctga atgaagccat accaaacgac gagcgtgaca ccacgatgcc   1140
tgcagcaatg gcaacaacgt tgcgcaaact attaactggc gaactactta ctctagcttc   1200
ccggcaacaa ttaatagact ggatggaggc ggataaagtt gcaggaccac ttctgcgctc   1260
ggcccttccg gctggctggt ttattgctga taaatctgga gccggtgagc gtgggtctcg   1320
cggtatcatt gcagcactgg ggccagatgg taagccctcc cgtatcgtag ttatctacac   1380 gacgggagt caggcaacta tggatgaacg aaatagacag atcgctgaga taggtgcctc   1440
actgattaag cattggtaac tgtcagacca gtttactca tatatacttt agattgattt   1500
aaaacttcat ttttaattta aaaggatcta ggtgaagatc cttttttgata atctcatgac   1560 caaaatccct taacgtgagt tttcgttcca ctgagcgtca gaccccgtag aaaagatcaa   1620
aggatcttct tgagatcctt ttttttctgcg cgtaatctgc tgcttgcaaa caaaaaaacc   1680
accgctacca gcggtggttt gtttgccgga tcaagagcta ccaactcttt ttccgaaggt   1740
aactggcttc agcagagcgc agataccaaa tactgtcctt ctagtgtagc cgtagttagg   1800
ccaccacttc aagaactctg tagcaccgcc tacatacctc gctctgctaa tcctgttacc   1860
agtggctgct gccagtggcg ataagtcgtg tcttaccggg ttggactcaa gacgatagtt   1920
accggataag gcgcagcggt cgggctgaac ggggggttcg tgcacacagc ccagcttgga   1980
gcgaacgacc tacaccgaac tgagatacct acagcgtgag ctatgagaaa gcgccacgct   2040
tcccgaaggg agaaaggcgg acaggtatcc ggtaagcggc agggtcggaa caggagagcg   2100
cacgagggag cttccagggg gaaacgcctg gtatctttat agtcctgtcg ggtttcgcca   2160
cctctgactt gagcgtcgat ttttgtgatg ctcgtcaggg gggcggagcc tatggaaaaa   2220
cgccagcaac gcggccttt tacggttcct ggccttttgc tggccttttg ctcacatgtt   2280
ctttcctgcg ttatcccctg attctgtgga taaccgtatt accgcctttg agtgagctga   2340
taccgctcgc cgcagccgaa cgaccgagcg cagcgagtca gtgagcgagg aagcggaaga   2400
gcgcctgatg cggtattttc tccttacgca tctgtgcggt atttcacacc gcatatatgg   2460
tgcactctca gtacaatctg ctctgatgcc gcatagttaa gccagtatac actccgctat   2520
cgctacgtga ctgggtcatg gctgcgcccc gacacccgcc aacacccgct gacgcgccct   2580
gacgggcttg tctgctcccg gcatccgctt acagacaagc tgtgaccgtc tccgggagct   2640
gcatgtgtca gaggttttca ccgtcatcac cgaaacgcgc gaggcagctg cggtaaagct   2700
catcagcgtg gtcgtgaagc gattcacaga tgtctgcctg ttcatccgcg tccagctcgt   2760
tgagtttctc cagaagcgtt aatgtctggc ttctgataaa gcgggccatg ttaagggcgg   2820
ttttttcctg tttggtcact gatgcctccg tgtaaggggg atttctgttc atgggggtaa   2880
tgataccgat gaaacgagag aggatgctca cgatacgggt tactgatgat gaacatgccc   2940
```

```
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg gcgataatgg cctgcttctc gccgaaacgt tggtggcgg    3360 gaccagtgac gaaggcttga gcgagggcgt gcaagattcc gaataccgca agcgacaggc    3420
cgatcatcgt cgcgctccag cgaaagcggt cctcgccgaa aatgacccag agcgctgccg    3480
gcacctgtcc tacgagttgc atgataaaga agacagtcat aagtgcggcg acgatagtca    3540
tgccccgcgc ccaccggaag gagctgactg ggttgaaggc tctcaagggc atcggtcgag    3600
atcccggtgc ctaatgagtg agctaactta cattaattgc gttgcgctca ctgcccgctt    3660
tccagtcggg aaacctgtcg tgccagctgc attaatgaat cggccaacgc gcggggagag    3720
gcggtttgcg tattgggcgc cagggtggtt tttcttttca ccagtgagac gggcaacagc    3780
tgattgccct tcaccgcctg gccctgagag agttgcagca agcggtccac gctggtttgc    3840
cccagcaggc gaaaatcctg tttgatggtg gttaacggcg ggatataaca tgagctgtct    3900
tcggtatcgt cgtatcccac taccgagata tccgcaccaa cgcgcagccc ggactcggta    3960
atggcgcgca ttgcgcccag cgccatctga tcgttggcaa ccagcatcgc agtgggaacg    4020
atgccctcat tcagcatttg catggtttgt tgaaaaccgg acatggcact ccagtcgcct    4080
tcccgttccg ctatcggctg aatttgattg cgagtgagat atttatgcca gccagcaga    4140 cgcagacgcg ccgagacaga acttaatggg cccgctaaca gcgcgatttg ctggtgaccc    4200
aatgcgacca gatgctccac gcccagtcgc gtaccgtctt catgggagaa aataatactg    4260
ttgatgggtg tctggtcaga gacatcaaga aataacgccg gaacattagt gcaggcagct    4320
tccacagcaa tggcatcctg gtcatccagc ggatagttaa tgatcagccc actgacgcgt    4380
tgcgcgagaa gattgtgcac cgccgcttta caggcttcga cgccgcttcg ttctaccatc    4440
gacaccacca cgctggcacc cagttgatcg gcgcgagatt taatcgccgc gacaatttgc    4500
gacggcgcgt gcagggccag actggaggtg caacgccaa tcagcaacga ctgtttgccc    4560
gccagttgtt gtgccacgcg gttgggaatg taattcagct ccgccatcgc cgcttccact    4620
ttttcccgcg ttttcgcaga aacgtggctg gcctggttca ccacgcggga aacggtctga    4680
taagagacac cggcatactc tgcgacatcg tataacgtta ctggtttcac attccaccc    4740 ctgaattgac tctcttccgg cgctatcat gccataccgc gaaaggtttt gcgccattcg    4800
atggtgtccg ggatctcgac gctctccctt atgcgactcc tgcattagga agcagcccag    4860
tagtaggttg aggccgttga gcaccgccgc cgcaaggaat ggtgcatgca aggagatggc    4920
gcccaacagt ccccggcca cggggcctgc caccatacc acgccgaaac aagcgctcat    4980
gagcccgaag tggcgagccc gatcttcccc atcggtgatg tcggcgatat aggcgccagc    5040
aaccgcacct gtggcgccgg tgatgccggc cacgatgcgt ccggcgtaga ggatcgagat    5100
ctcgatcccg cgaaattaat acgactcact atagggaat tgtgagcgga taacaattcc    5160
cctctagaaa taattttgtt aactttaag aaggagatat acatatgaaa tacctgctgc    5220
cgaccgctgc tgctggtctg ctgctcctcg ctgcccagcc ggcgatggcc atggatgcgg    5280
```

```
cggaggaagg cgaactggcg gcggaactgg cggaaaaagc ggcggaagaa ggtgaactgg     5340
cggcggaact ggcggagaag gcggcggagg aaggtgaatt agctgcggag ttagctgaga     5400
aagcggcgga ggaaggcgag ctggcggcgg agctggcgga gaaggcggcg gaggaaggtg     5460
aacttgctgc ggagttagcc gaaaaagctg ctgaggaagg cgaattagct gcggagcttg     5520
ctgaaaaggc tgctgaggaa ggtgaattag ccgcggagtt agccgagaaa gctgctgagg     5580
aaggcgagtt agctgcggag ttagcagaaa aggctgccga ggaaggtgaa ttagcagcgg     5640
agttagcaga aaaagctgcc gaggaaggcg aattagccgc ggagcttgct gaaaaagctg     5700
cagaggaagg tgaattagcg gctgagttag ccgaaaaagc cgctgaggaa ggcgaacttg     5760
ctgcggagct tgctgagaag gctgctgagg aaggtgaact gccgcggag ttagcagaga     5820 aagctgccga ggaaggcgag ttagccgcgg agttagcgga aaaagctgcg gaggaaggtg     5880
aactcgctgc ggagttagcg gagaaagctg cagaggaagg cgaattagca gcggagcttg     5940
ctgagaaagc tgctgaggaa ggtgaactag cggcggagct tgccgaaaaa gccgccgagg     6000
aaggcgaact tgccgcggag cttgccgaga aggctgcgga ggaaggtgaa ctggctgctg     6060
agttagccga gaaagccgct gaggaaggcg agcttgctgc ggagcttgcc gagaaagctg     6120
cagaggaagg tgaacttgca gcggagcttg cagaaaaagc cgcagaggaa ggcgaacttg     6180
cagcggagct cgctgaaaag gccgctgagg aaggtgaact cgccgcggag cttgcagaga     6240
aagctgcgga ggaaggcgaa ttagcggcgg agctggcgga aaaggccgcc gaggaaggtg     6300
aacttgcggc tgagttagca gaaaaagccg cggaggaagg cgaattggct gctgagctgg     6360
cggaaaaggc agctgaggaa ggtgaactgg ccgctgagtt agcagagaaa gccgccgagg     6420
aaggcgagct tgccgcggag cttgcggaaa aagcagccga ggaaggtgaa ctcgcagcgg     6480
agcttgcgga gaaagctgcg gaggaaggcg agttagcagc tgaactggcg gaaaagctcg     6540
agcaccacca ccaccaccac tgagatccgg ctgctaacaa agcccgaaag gaagctgagt     6600
tggctgctgc caccgctgag caataactag cataacccct tggggcctct aaacgggtct     6660
tgagggtttt tttgctgaaa ggaggaacta tatccggat                           6699
```